(12) United States Patent
Nishikubo et al.

(10) Patent No.: US 7,705,189 B2
(45) Date of Patent: Apr. 27, 2010

(54) CALIXARENE COMPOUND, PROCESS FOR PRODUCING THE SAME, INTERMEDIATE THEREFOR, AND COMPOSITION THEREOF

(75) Inventors: Tadatomi Nishikubo, Fujisawa (JP); Hiroto Kudou, Yokohama (JP); Kouji Mitani, Chuo-ku (JP)

(73) Assignees: JSR Corporation, Tokyo (JP); Kanagawa University, Yokohama-shi (JP)

( * ) Notice: Subject to any disclaimer, the term of this patent is extended or adjusted under 35 U.S.C. 154(b) by 729 days.

(21) Appl. No.: 10/588,313

(22) PCT Filed: Feb. 4, 2005

(86) PCT No.: PCT/JP2005/001717

§ 371 (c)(1),
(2), (4) Date: Jan. 11, 2007

(87) PCT Pub. No.: WO2005/075398

PCT Pub. Date: Aug. 18, 2005

(65) Prior Publication Data

US 2007/0123736 A1    May 31, 2007

(30) Foreign Application Priority Data

Feb. 4, 2004   (JP)   ............... 2004-028400
Feb. 4, 2004   (JP)   ............... 2004-028404
Feb. 13, 2004  (JP)   ............... 2004-036530

(51) Int. Cl.
*C07C 43/20*   (2006.01)
*C07C 39/12*   (2006.01)

(52) U.S. Cl. ............... 568/632; 568/636; 568/719

(58) Field of Classification Search ............... 568/632, 568/633, 719
See application file for complete search history.

(56) References Cited

FOREIGN PATENT DOCUMENTS

| JP | 57 17661 | 1/1982 |
| JP | 5 27430 | 2/1993 |

OTHER PUBLICATIONS

Gutsche et al. Calixarenes. Journal of Organic Chemistry, 1978, 43 (25) p. 4905-4906.*

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

A novel calixarene compound, a method for manufacturing the same, an intermediate of the calixarene compound, and a composition comprising the same are provided. The calixarene compound is expected to be useful as an inclusion compound and, if functional groups are introduced, can be used for a curable composition and a photoresist and as an inclusion compound. The calixarene compound is shown by following formula (1):

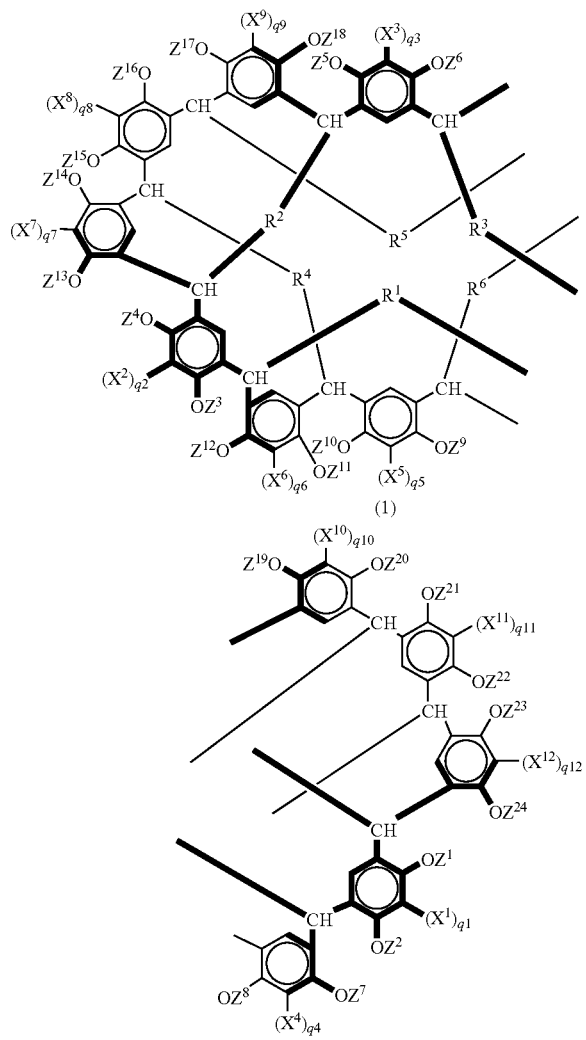

[Formula 1]

(1)

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1-8 carbon atom content, or two adjacent Zs in combination represent a substituted or unsubstituted alkylene group having 1 to 8 carbon atoms; $q^1$ to $q^{12}$ individually represent an integer of 0 or 1.

22 Claims, 6 Drawing Sheets

NOTE: DPSP 5mol%

◆ : DPSP 5mol%
▲ : DPSP 1mol%

NOTE:DPSP 5mol%

◆ : DPSP 5mol%
▲ : DPSP 1mol%

CALIXARENE COMPOUND, PROCESS FOR PRODUCING THE SAME, INTERMEDIATE THEREFOR, AND COMPOSITION THEREOF

FIELD OF THE INVENTION

The present invention relates to a novel calixarene compound, a method for manufacturing the calixarene compound, an intermediate of the calixarene compound, and a composition containing the same. More particularly, the present invention relates to a novel calixarene compound that is expected to be useful as an inclusion compound and the like and can be easily provided with a function by introducing a functional group, a method for manufacturing the calixarene compound, an intermediate of the calixarene compound, and also to a novel calixarene compound (derivative) that is expected to be useful as a curable composition, a resist, or an inclusion compound, and to a curable composition and a resist composition containing the derivative.

BACKGROUND OF THE INVENTION

A calixarene compound is a cyclic oligomer generally obtained by condensation of a phenol compound (e.g. phenol, resorcinol) and an aldehyde compound. In recent years, the calixarene compound is gaining attention as the third inclusion compound next to crown ether and cyclodextrin in the field of host-guest chemistry.

The calixarene compound is regarded as an outstanding functional material due to the possession of many hydroxyl groups in the molecule, excellent thermal stability, high glass transition temperature and high melting point, and film-formability according to the structure. For example, application to an electron-beam negative-tone photo resist using p-methylcalix[6]arene hexa-acetate (e.g. See Non-Patent Document 1) and application to a negative-tone alkali development-type resist containing calix[4]resorcin arene, a crosslinking agent, and a photoacid generator (e.g. See Non-Patent Document 2) have been reported. Moreover, synthesis of calixarene derivatives by the introduction of radically polymerizable functional groups and cationically polymerizable functional groups for the purpose of applying the calixarene compound to a high performance photocurable material and the introduction of protective groups for the purpose of application to a high resolution resist material, as well as the evaluation of photo-reactivity of the calixarene derivatives have been reported (e.g. See Non-Patent Document 3 to 5). Synthesis of p-alkylcalix[n]arene derivatives having various cationically-polymerizable functional groups and studies on the cationic photopolymerization of such derivatives have been reported (e.g. See Non-Patent Document 6).

In addition, among the calixarene compounds, various studies have been undertaken on calixresorcinolarene compounds which are the condensates of a resorcinol compound and an aldehyde compound regarding their capability of including large guest compounds. A number of derivatives having large and deep holes have been synthesized by chemical modification of the resorcinol ring.

For example, a basket-type cavitand with a firmly fixed cone conformation can be obtained by crosslinking hydroxyl group pairs of adjacent resorcinol rings via a covalent bond. Alkylation using a dihalomethane (See Non-Patent Document 7) and silylation using a dialkyl dichlorosilane (See Non-Patent Document 8) have been reported. As resorcinol compounds, derivatives having a functional group such as CHO (See Non-Patent Document 9), OH (See Non-Patent Document 10) or $CO_2R$ (See Non-Patent Document 11) have been reported. Furthermore, possibility of obtaining a capsule-type carcerand in which two or more cavitands having suitable functional groups are combined via an $S_N2$ reaction has also been reported (See Non-Patent Document 12). However, since there are no more reactive groups left in these cavitants, further chemical modification of these cavitants is difficult.

(Non-Patent Document 1) Y. Ochiai, S. Manako, H. Yamamoto, T. Teshima, J. Fujita, E. Nomura: J. Photopolymer. Sci. Tech. 13, 413 (2000)

(Non-Patent Document 2) T. Nakayama, M. Nomura, K. Haga, M. Ueda: Bull. Chem. Soc. Jpn., 71, 2979 (1998)

(Non-Patent Document 3) T. Nishikubo, A. Kameyama, and H. Kudo, K. Tsutsui: J. Polym. Sci. Part. Part A. Polym. Chem, 39, 1293 (2002)

(Non-Patent Document 4) T. Nishikubo, A. Kameyama, and H. Kudo: Polym J., 35, 213 (2003)

(Non-Patent Document 5) T. Nishikubo, A. Kameyama, and H. Kudo: Am. Chem. Soc, 31, 363

(Non-Patent Document 6) K. Tsutsui, S. Kishimoto, A. Kameyama, T. Nishikubo: Polym. Prep. Jpn., 37, 1805 (1999)

(Non-Patent Document 7) J. R. Moran, S. karbach, and D. J. Cram, J. Am. Chem. Soc., 104, 5826, (1982)

(Non-Patent Document 8) D. J. Cram, K. D. Stewart, I. Goldberg, and K. N. Trueblood, J, Am. Chem. Soc., 107, 2574, (1985)

(Non-Patent Document 9) M. L. C. Quan, and D. J. Cram, J, Am. Chem. Soc., 113, 2754, (1991)

(Non-Patent Document 10) J. C. Sherman, and D. J. Cram, J, Am. Chem. Soc., 111, 4527, (1989)

(Non-Patent Document 11) J. C. Sherman and D. J. Cram, J, Am. Chem. Soc., 111, 4527, (1989)

(Non-Patent Document 12) P. Timmerman, W. Verboom, F. C. J. M. van Veggel, W. Hoorn, and D. N. Reoinhoudt, Angew. Chem. Int. Ed. Engl., 33, 1292, (1994)

DISCLOSER OF THE INVENTION

The present invention is characterized by providing a novel calixarene compound having a carcerand-like stereostructure and being chemically modified with ease, a method for manufacturing the calixarene compound, an intermediate of the calixarene compound, a novel calixarene compound (derivative) which is a derivative of the calixarene compound being applicable to a curable composition, a photoresist, and an inclusion compound, and a composition using the derivative.

That is, the present invention provides a calixarene compound shown by following formula (1):

[Formula 1]

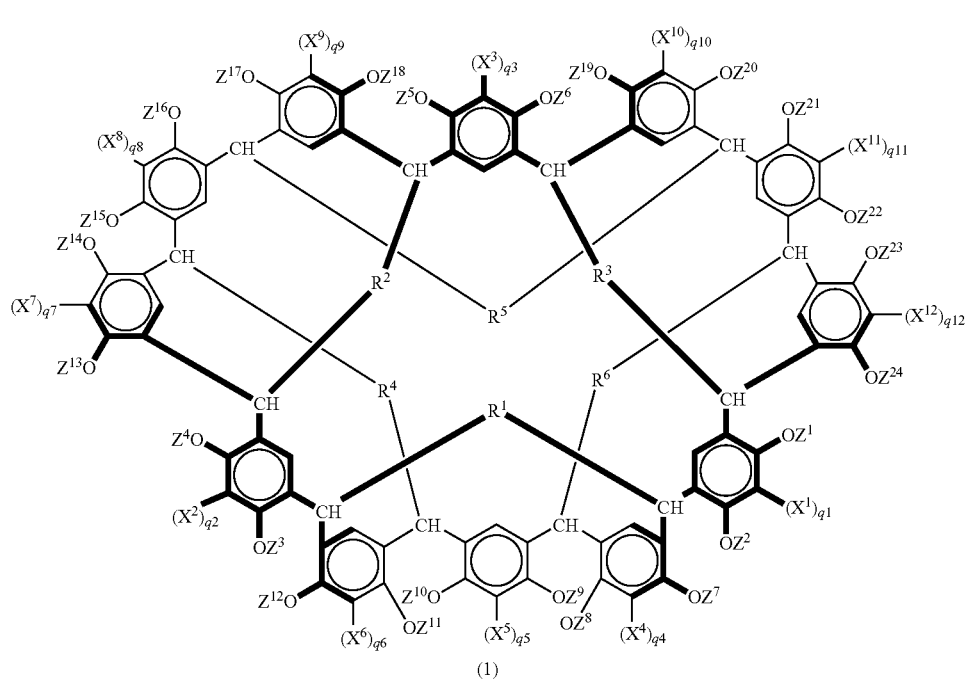

(1)

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms; a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content, or two adjacent Zs in combination represent a substituted or unsubstituted alkylene group having 1 to 8 carbon atoms; $q^1$ to $q^{12}$ individually represent an integer of 0 or 1.

In the formula (1), $X^1$ to $X^{12}$ are preferably methyl groups. In addition, $q^1$ to $q^{12}$ are preferably 0. Further, $R^1$ to $R^6$ are individually an alkylene group having 3, 5, 7, or 8 carbon atoms.

A compound having hydrogen atoms for all of the $Z^1$ to $Z^{24}$ groups in the formula (1) is preferable as a calixarene compound that can be chemically modified with ease. A compound having a group other than a hydrogen atom for at least one of the $Z^1$ to $Z^{24}$ groups is preferable as a derivative of calixarene compound. A compound having a polymerizable functional group, particularly a polymerizable unsaturated group and/or a cyclic ether group for at least one of the $Z^1$ to $Z^{24}$ groups is preferable for use in a curable composition. A compound having an alkali-soluble group, particularly a group selected from the group consisting of a carboxyl group, amino group, sulfonamide group, sulfonic acid group, and phosphoric acid group for at least one of the $Z^1$ to $Z^{24}$ groups is preferable for use as a resist composition. Furthermore, it is desirable that at least one of the $Z^1$ to $Z^2$ groups contains both a polymerizable functional group and an alkali-soluble group.

The present invention also provides an intermediate of a calixarene compound shown by at least one of the following formula (2) to (8):

[Formula 2]

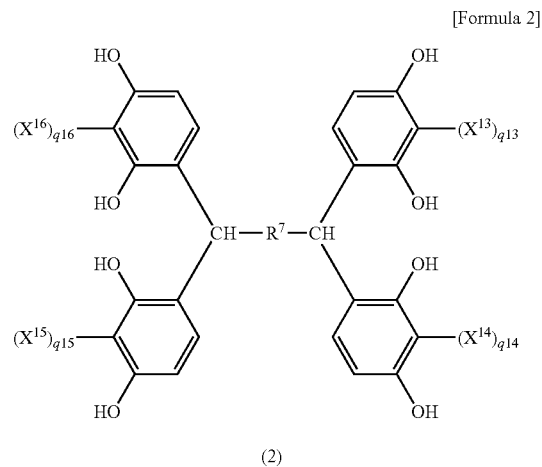

(2)

wherein $R^7$ represents a substituted or unsubstituted alkylene group having 1 to 8 carbon atoms; $X^{13}$ to $X^{16}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{13}$ to $q^{16}$ individually represent an integer of 0 or 1.

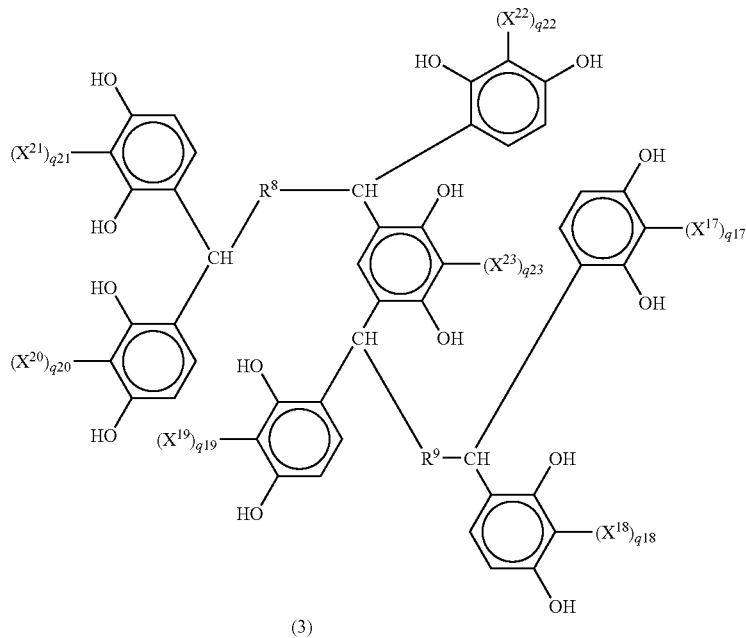

(3)

wherein $R^8$ and $R^9$ individually represent a substituted or unsubstituted alkylene group having 1 to 8 carbon atoms; $X^{17}$ to $X^{23}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{17}$ to $q^{23}$ individually represent an integer of 0 or 1.

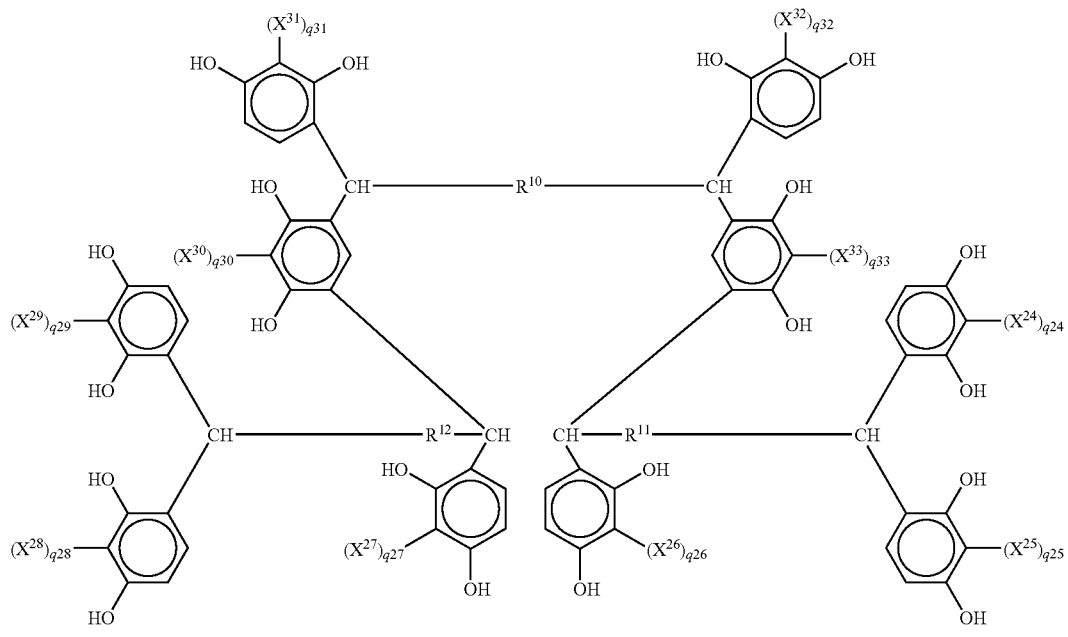

(4)

wherein $R^{10}$ to $R^{12}$ individually represent a substituted or unsubstituted alkylene group having 1 to 8 carbon atoms; $X^{24}$ to $X^{33}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $q^{24}$ to $q^{33}$ individually represent an integer of 0 or 1.

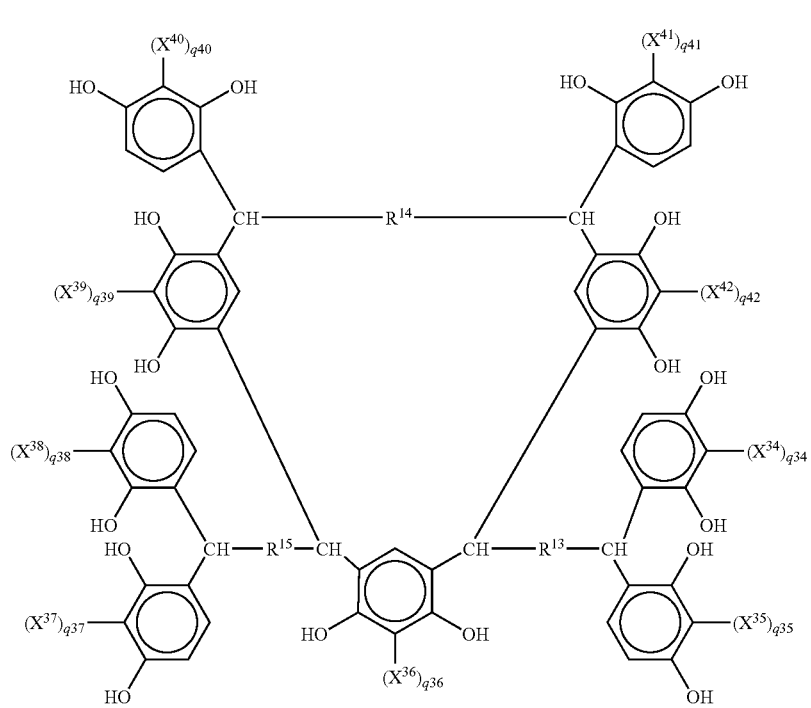

[Formula 5]

(5)

wherein $R^{13}$ to $R^{15}$ individually represent a substituted or unsubstituted alkylene group having 1 to 8 carbon atoms; $X^{34}$ to $X^{42}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{34}$ to $q^{42}$ individually represent an integer of 0 or 1.

[Formula 6]

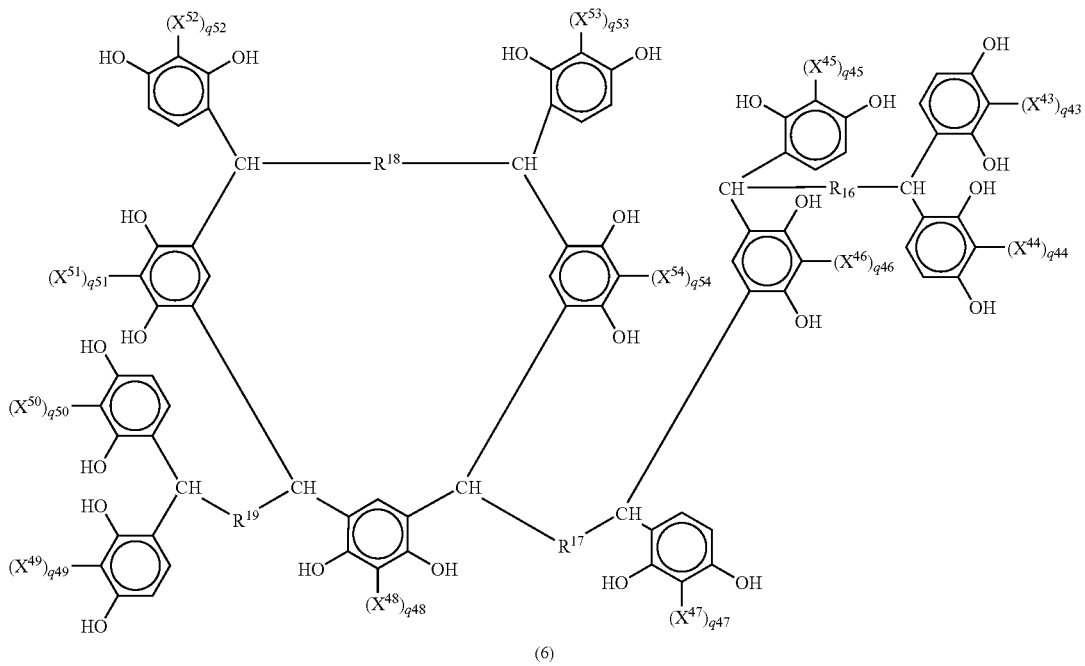

(6)

wherein $R^{16}$ to $R^{19}$ individually represent a substituted or unsubstituted alkylene group having 1 to 8 carbon atoms; $X^{43}$ to $X^{54}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{43}$ to $q^{54}$ individually represent an integer of 0 or 1.

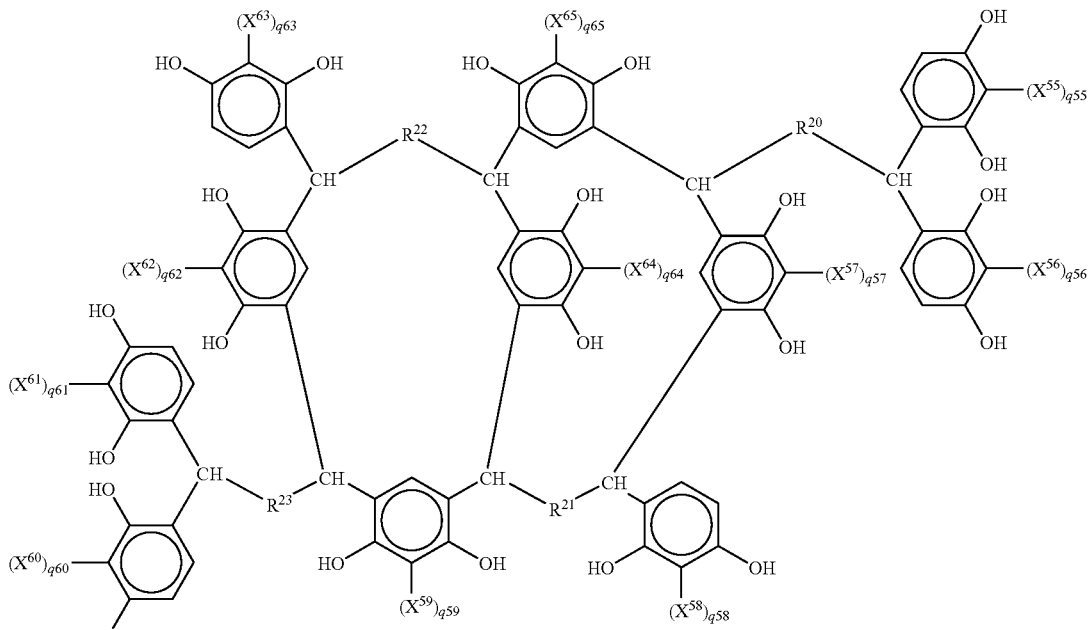

[Formula 7]

(7)

wherein $R^{20}$ to $R^{23}$ individually represent a substituted or unsubstituted alkylene group having 1 to 8 carbon atoms; $X^{55}$ to $X^{65}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{55}$ to $q^{65}$ individually represent an integer of 6 or 1.

[Formula 8]

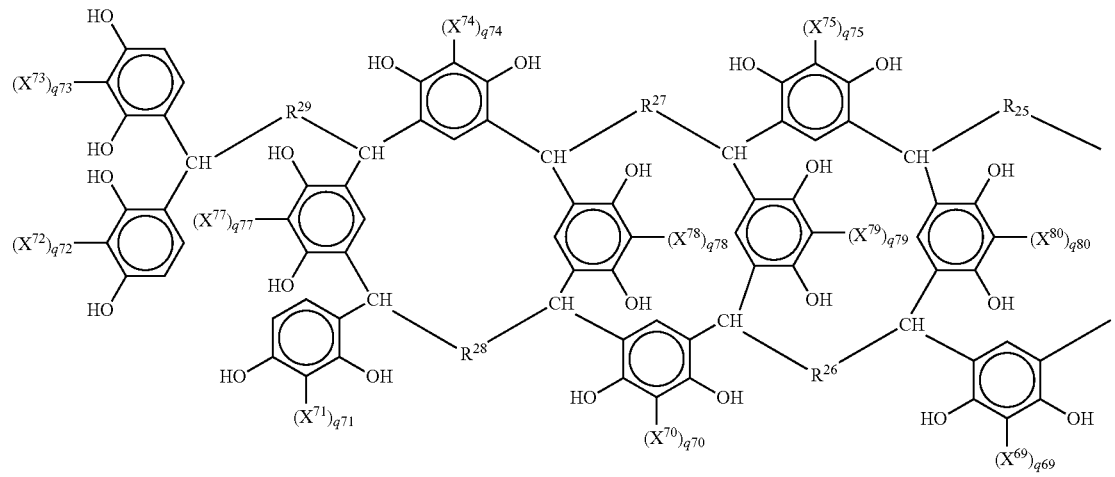

(8)

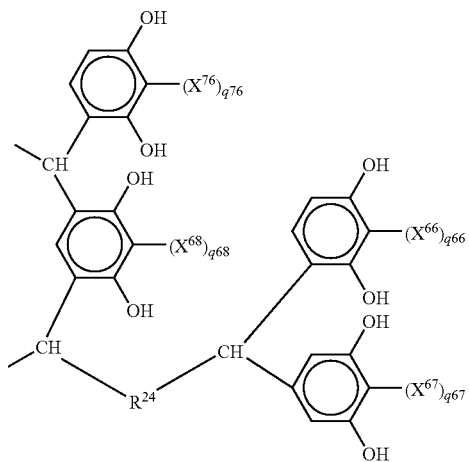

wherein $R^{24}$ to $R^{29}$ individually represent a substituted or unsubstituted alkylene group having 1 to 8 carbon atoms; $X^{66}$ to $X^{80}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{66}$ to $q^{80}$ individually represent an integer of 0 or 1.

In the formulas (2) to (8), $X^{13}$ to $X^{80}$ are preferably methyl groups. In addition, $q^{13}$ to $q^{80}$ are preferably 0. Further, $R^7$ to $R^{29}$ are individually an alkylene group having 3, 5, 7, or 8 carbon atoms in a preferable embodiment.

a substituted or unsubstituted aralkyl group having 7 to 10 carbon atoms, a substituted or unsubstituted alkoxyl group having 1 to 10 carbon atoms, or a substituted or unsubstituted phenoxy group; and $q^{81}$ is an integer of 0 or 1.

[Formula 10]

$$OHC\text{—}R^{30}\text{—}CHO \quad (10)$$

wherein $R^{30}$ is a substituted or unsubstituted alkylene group having 1 to 8 carbon atoms.

In the formula (9), $X^{81}$ is preferably a methyl group, and $q^{81}$ is preferably 0. In the formula (10), $R^{30}$ is preferably an alkylene group having 3, 5, 7, or 8 carbon atoms.

The present invention further provides a composition comprising a calixarene compound of the formula (1) and a solvent which can dissolve the calixarene compound:

[Formula 11]

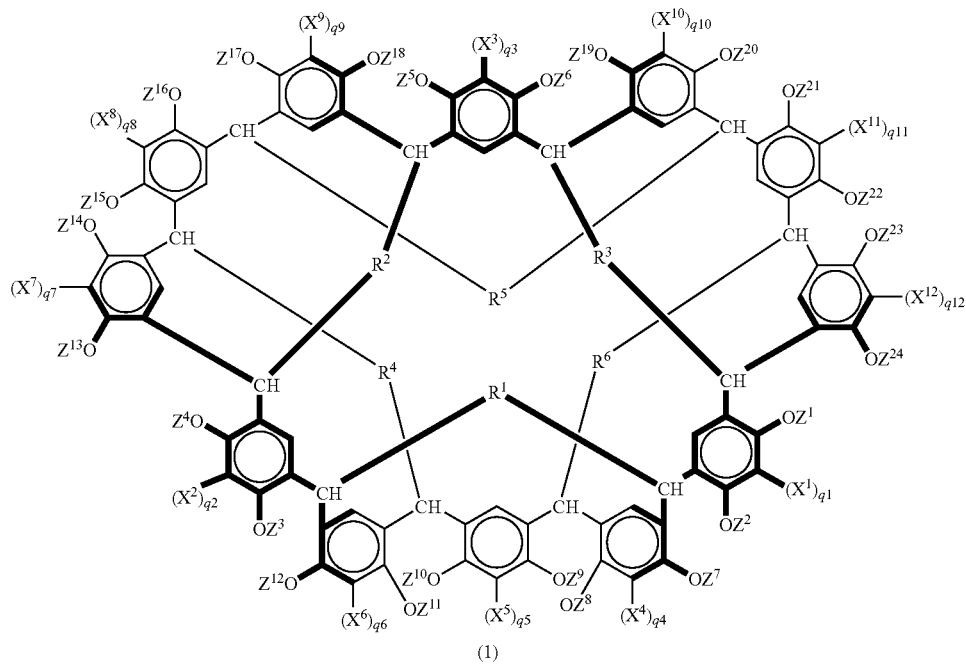

(1)

The present invention further provides a method for manufacturing a calixarene compound comprising condensing at least one compound shown by the formula (9) and at least one compound shown by the formula (10):

[Formula 9]

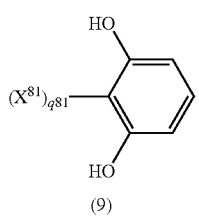

(9)

wherein $X^{81}$ represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content, or two adjacent Zs in combination represent a substituted or unsubstituted alkylene group having 1 to 8 carbon atoms; $q^1$ to $q^{12}$ individually represent an integer of 0 or 1.

A composition containing a calixarene compound having a polymerizable functional group for at least one of the $Z^1$ to $Z^{24}$ groups in the formula (1) and a polymerization initiator is preferable as a curable composition. A composition containing a calixarene compound having an alkali-soluble group for at least one of the $Z^1$ to $Z^{24}$ groups in the formula (1) is preferable as a resist composition.

A calixarene compound having hydrogen atoms for all of the $Z^1$ to $Z^{24}$ groups in the formula (1) is expected to be useful as an inclusion compound due to the carcerand-like stereostructure and due to ease of being provided with a function by introduction of a functional group. A calixarene compound having a group other than the hydrogen atom for at least one of the $Z^1$ to $Z^{24}$ groups in the formula (1) (hereinafter referred to as a calixarene derivative) has high heat resistance and is expected to be useful in curable compositions and resist compositions, as an inclusion compound, and in a wide variety of fields such as application as an intermediate for producing calixarene derivatives possessing higher functions. The intermediate material of a calixarene compound can suitably be used as an intermediate material of the above-mentioned calixarene compound. The method for manufacturing a calixarene compound can suitably be used as a method for manufacturing the above-mentioned calixarene compound. The above-mentioned curable composition containing the calixarene compound can form a film with a high heat resistance due to its improved film-formability.

BEST MODE FOR CARRYING OUT THE INVENTION

Figure 1:
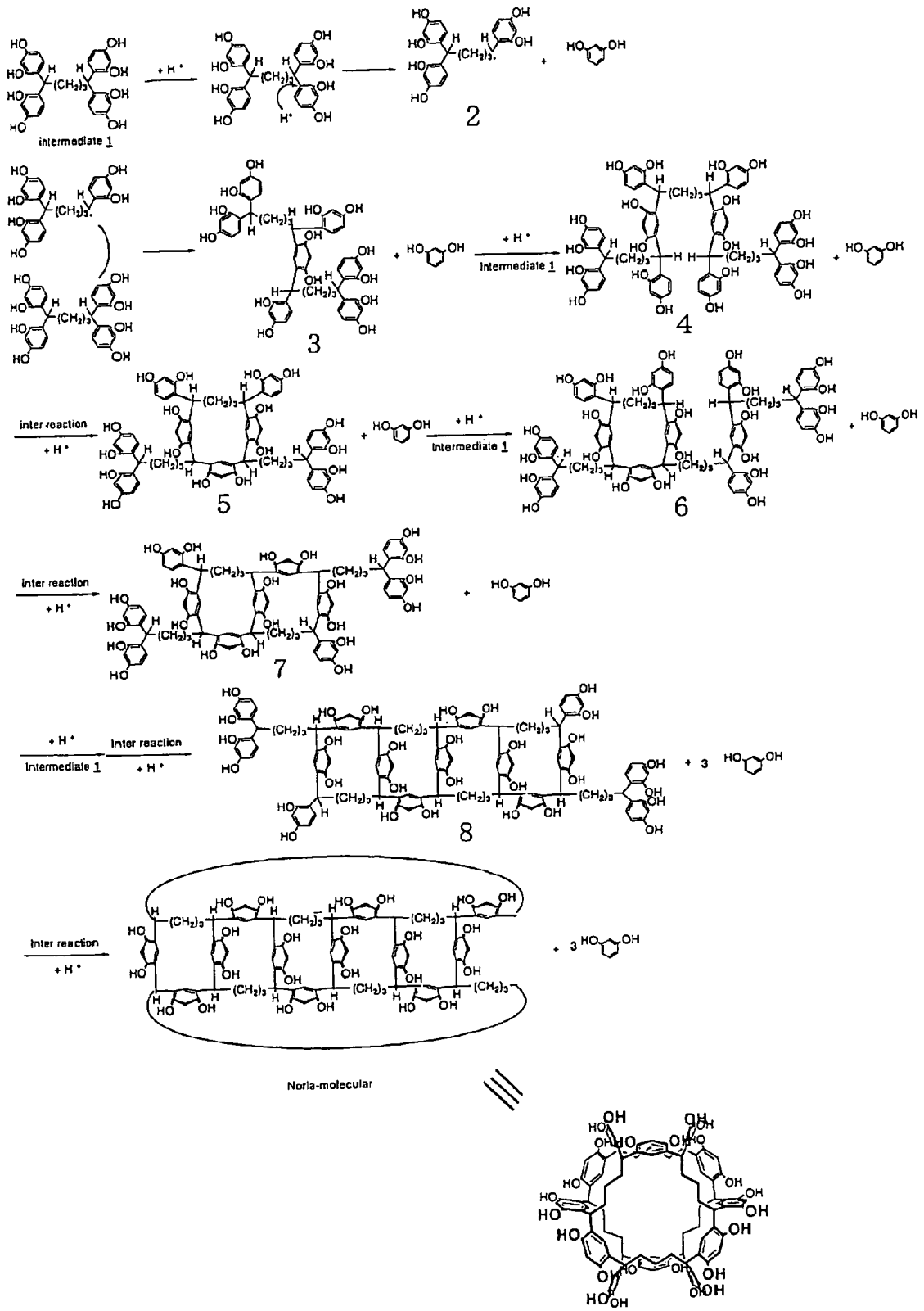
FIG. 1 shows one example of the reaction mechanism and intermediates for synthesizing the calixarene compound of the present invention.

The calixarene compound, the method for manufacturing, the intermediate, and the composition of the present invention will be described below in detail for specific embodiments, which, however, should not be construed as limiting the present invention.

The calixarene compound of the present invention is shown by the following formula (1):

[Formula 12]

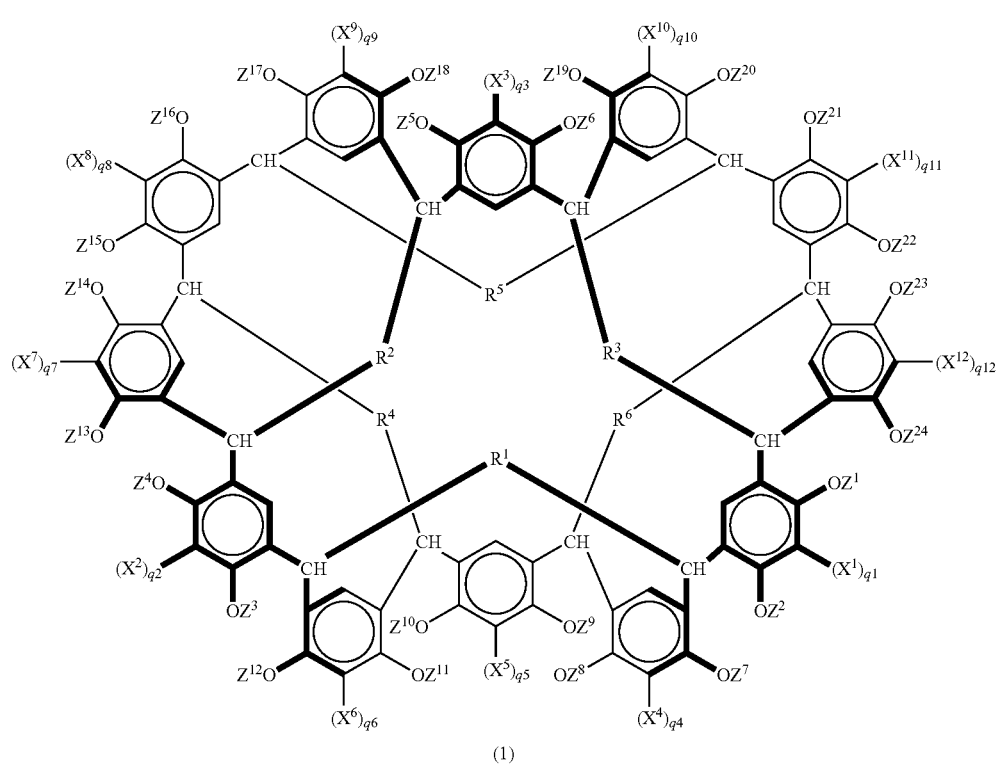

(1)

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content, or two adjacent Zs in combination represent a substituted or unsubstituted alkylene group having 1 to 8 carbon atoms; $q^1$ to $q^{12}$ individually represent an integer of 0 or 1.

Among the calixarene compounds of the formula (1), a compound in which all of the $Z^1$ to $Z^{24}$ groups are hydrogen atoms, that is, the calixarene compound of the following formula (13) will be first described.

only enables the calixarene compound to be suitably used as an inclusion compound, but also makes it easy for the compound to be provided with functions by chemical modification of hydroxyl groups.

Substituents ($X^1$ to $X^{12}$) other than the hydroxyl groups in any aromatic ring may be either present or not present. However, various substituents may be provided according to objects. As the substituents ($X^1$ to $X^{12}$), a substituted or unsubstituted alkyl group having 1 to 10 carbon atoms, a substituted or unsubstituted alkenyl group having 2 to 10 carbon atoms, a substituted or unsubstituted alkynyl group having 2-10 carbon atoms, a substituted or unsubstituted aralkyl group having 7 to 10 carbon atoms, a substituted or unsubstituted alkoxyl group having 1 to 10 carbon atoms, and a substituted or unsubstituted phenoxy group can be given. The substituents ($X^1$ to $X^{12}$) may be either the same or different from each other.

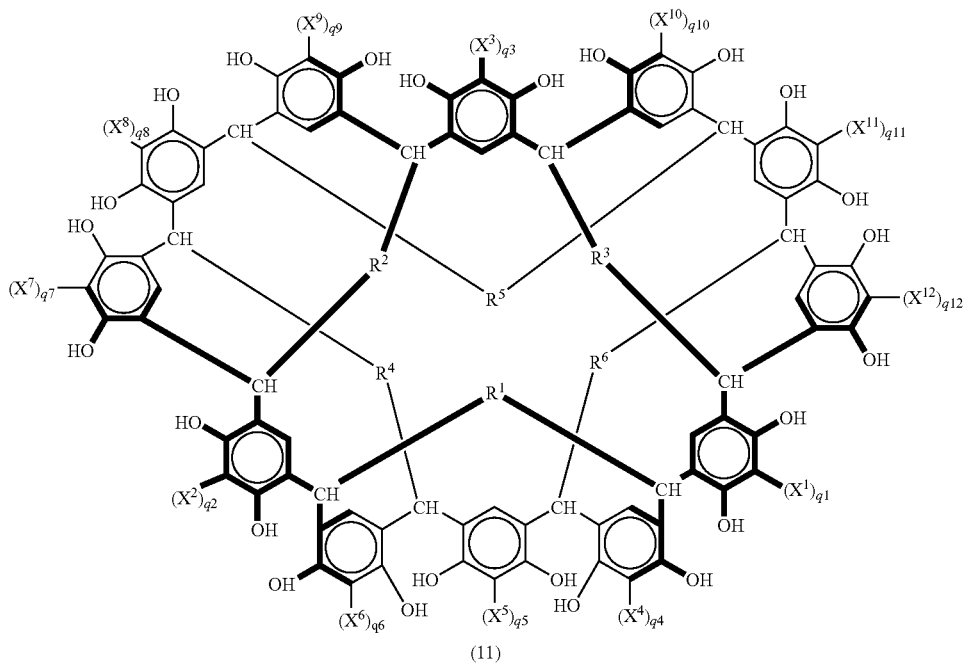

[Formula 13]

(11)

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $q^1$ to $q^{12}$ individually represent an integer of 0 or 1.

In the calixarene compound of the formula (11), the aromatic ring is a 1-substituted or unsubstituted resorcinol ring. Since the aromatic ring is a 1-substituted or unsubstituted resorcinol ring, the conformation is easily fixed, which not When the aromatic ring is a 1-substituted resorcinol ring, the aromatic ring portion preferably has the structure shown by the formula (12), wherein X is preferably a methyl group.

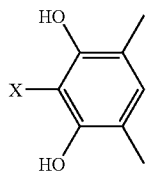

[Formula 14]

(12)

In the calixarene compound shown by the formula (11), $R^1$ to $R^6$ are individually a substituted or unsubstituted alkylene group having 1 to 8 carbon atoms. Of these alkylene groups, substituted or unsubstituted alkylene groups having an alkylene group with 3, 5, 7, or 8 carbon atoms as a basic skeleton are preferable due to easy formation of a ring structure. Moreover, a cyclic trimer can be obtained at a very high yield when all groups $R^1$ to $R^6$ are linear alkylene groups having three carbon atoms.

Such a calixarene compound shown by the formula (11) can be used as is or after being provided with functions as a highly heat resistant inclusion compound or as a component for a curable material or resist material. Furthermore, it is possible to form a cylindrical structure by piling a plurality of the calixarene compounds. If a conductive polymer such as polyaniline is located in the internal hollow portion of the cylindrical structure, very minute conductive channels surrounded by the insulating calixarene compound can be formed and applied to various fields such as the field of ultrafine electronic circuit.

Next, a method for manufacturing the aforementioned calixarene compound will be described. The calixarene compound as described above can be obtained by condensing a compound of the following formula (9) and a compound of the following formula (10).

[Formula 15]

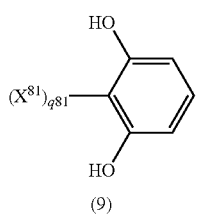

(9)

wherein $X^{81}$ represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{81}$ is an integer of 0 or 1.

[Formula 16]

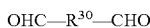
$$OHC-R^{30}-CHO \qquad (10)$$

wherein $R^{30}$ represents a substituted or unsubstituted alkylene group having 1 to 8 carbon atoms.

The compound of the formula (9) is a 1-substituted or unsubstituted dihydroxy benzene, and $X^{81}$ and $q^{81}$ in the formula (9) correspond respectively to $X^1$ to $X^{12}$ and $q^1$ to $q^{12}$ in the formula (11). As specific examples of the compound of the formula (9), resorcinol, 2-methyl resorcinol, and 2-butyl resorcinol can be given. It is preferable to use at least one of these compounds. Of these, resorcinol and 2-methyl resorcinol are particularly preferable.

The compound of the formula (10) is a dialdehyde compound and, $R^{30}$ in the formula (10) corresponds to $R^1$ to $R^6$ in the formula (11). As specific examples of the compound of the formula (10), 1,5-pentanedial, 1,7-hexanedial, 1,9-nonanedial, and 1,10-decanedial can be given. Use of at least one of these compounds is preferable.

Although there are no specific limitations on the ratio of the compound shown by the formula (9) (hereinafter referred to as compound (A)) to the compound shown by the formula (10) (hereinafter referred to as compound (B)), the molar ratio of the compound (B)/compound (A) is preferably in the range of 0.05 to 0.85, more preferably 0.075 to 0.6, and particularly preferably 0.1 to 0.3 from the viewpoint of the yield. Although there are no specific limitations on the monomer concentration (the total concentration of the compound (A) and compound (B)), the concentration is preferably 2 mol/l or more, more preferably 4 mol/l or more, and particularly preferably in the range of 4 to 10 mol/l from the viewpoint of the yield.

These compounds are dehydrated to condense in a solvent in the presence of a catalyst. As the catalyst, acid catalysts and the like can be given.

The reaction proceeds sequentially by dehydrating and condensing these compounds, then finally producing a calixarene compound. The intermediate compounds are produced, as the following process for producing, for example. An intermediate compound 1 shown by the formula (2) is produced by condensation of four molecules of the compound (A) and one molecule of the compound (B). Two molecules of the intermediate compound 1 produce the intermediate compound 3 shown in the formula (3) by condensation reaction with removal of compound (A). Then, an intermediate compound 4 shown in the formula (4), an intermediate compound 5 shown in the formula (5), an intermediate compound 6 shown in the formula (6), an intermediate compound 7 shown in the formula (7) and an intermediate compound 8 shown in the formula (8) are sequentially produced by condensation reaction in molecules or with the intermediate compound 1 with removal of compound (A). As a result, the calixarene compound shown in the formula (11) can be produced.

One specific example of the process for producing the intermediate compounds when resorcinol was used as the compound (A) and pentanedial (glutaraldehyde) was used as the compound (B) is shown in FIG. 1.

Since these intermediate compounds can be removed in a stable manner during the reaction, the calixarene compound can also be manufactured using these intermediate compounds as raw materials. Therefore, the above-mentioned intermediate compounds can also suitably be used as raw materials for manufacturing the calixarene compound.

Next, a calixarene derivative (I) of the formula (1) in which at least one of the $Z^1$ to $Z^{24}$ groups is a group other than hydrogen atom and $Z^1$ to $Z^{24}$ are monovalent groups which are not bonded to each other will be described.

[Formula 17]

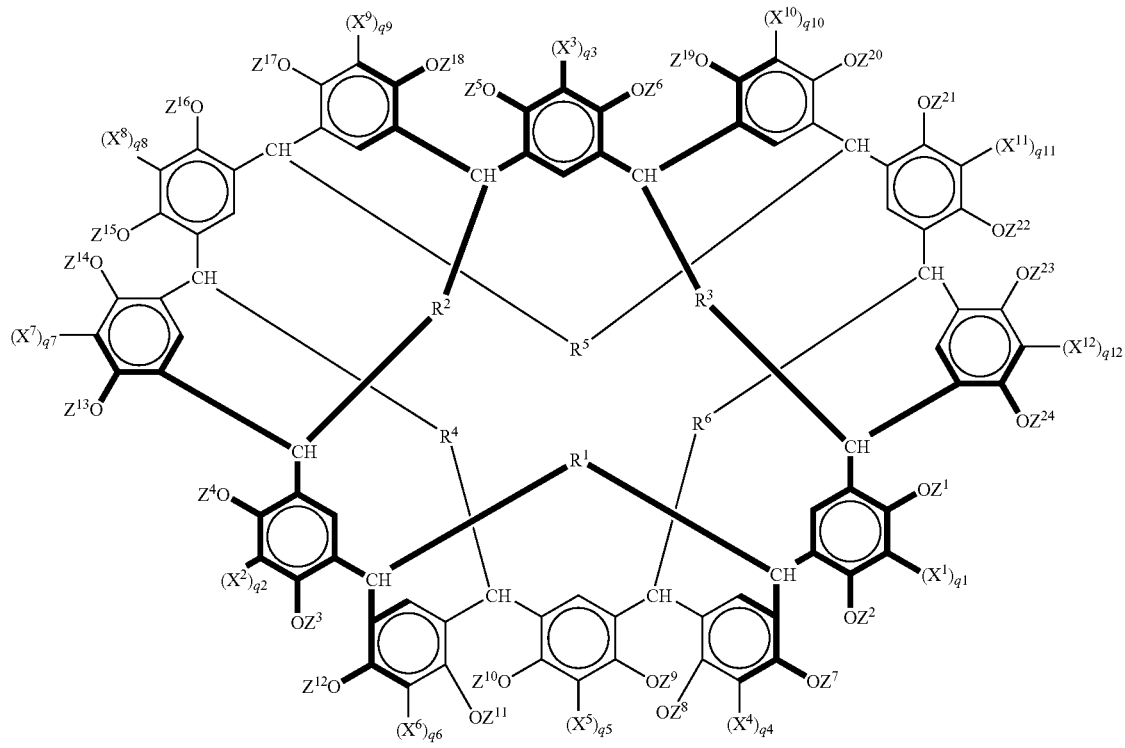

(1)

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content (provided that at least one of $Z^1$ to $Z^{24}$ is a group other than hydrogen atom); $q^1$ to $q^{12}$ individually represent an integer of 0 or 1.

In one of the preferred embodiments of the calixarene derivative (I), at least one of the groups $Z^1$ to $Z^{24}$ has a polymerizable functional group. The calixarene derivative (I) containing a polymerizable functional group can be used in a curable composition. In addition, such a polymerizable functional group improves the solubility in solvents and film-formability.

As examples of the polymerizable functional group, groups having a polymerizable unsaturated structure and groups having a cyclic ether structure can be given. As specific examples, a vinyl group, vinylidene group, acryloyl group, methacryloyl group, substituted or unsubstituted glycidyl group, substituted or unsubstituted oxetanyl group, and substituted or unsubstituted Spiro ortho ester groups can be given.

Although it is sufficient for the calixarene derivative (I) in this embodiment to have at least one polymerizable functional group mentioned above, the calixarene derivative (I) preferably contains an additional number of polymerizable functional groups in order to increase the curing speed. Specifically, the calixarene derivative (I) preferably has one or more, particularly preferably two, polymerizable functional groups in one aromatic ring.

In another preferred embodiment of the calixarene derivative (I), at least one of the $Z^1$ to $Z^{24}$ groups has an alkali-soluble group. The calixarene derivative (I) containing such a group can suitably be used in a resist composition. For example, after crosslinking by reacting the alkali-soluble group with a crosslinking agent such as a polyfunctional vinyl ether compound, a specific area is irradiated with light in the presence of a photoacid generator to be hydrolyzed to become alkali-soluble. Then, that specific area is dissolved in an alkaline solution and removed to form a specific uneven pattern. In addition, introducing such a group can improve the film-formability.

Furthermore, the presence of both the polymerizable functional group and alkali-soluble group is preferable for the calixarene derivative (I) to be suitably used in a photoresist composition and the like. For example, after forming a film of the calixarene derivative (I), a specific area is cured by being irradiated with light. Then, the other area is dissolved in an alkaline solution and removed to form a specific uneven pattern.

Preferable alkali-soluble groups include a carboxyl group, amino group, sulfonamide group, sulfonic group, and phosphate group.

Although it is sufficient for the calixarene derivative (I) in this embodiment to have at least one alkali-soluble group mentioned above, the calixarene derivative (I) preferably contains an additional number of alkali-soluble groups in order to increase solubility in an aqueous alkaline solution. Specifically, the calixarene derivative (I) preferably has one or more, particularly preferably two, alkali-soluble groups in one aromatic ring.

Furthermore, to produce a calixarene derivative (I) containing a larger number of polymerizable functional groups and alkali-soluble groups, it is preferable that at least one of the $Z^1$ to $Z^{24}$ groups contains both a polymerizable functional group and an alkali-soluble group.

In still another preferred embodiment of the calixarene derivative (I), at least one of the $Z^1$ to $Z^{24}$ groups has a substituted alkyl group in which the alkyl chain has 1 to 8 carbon atoms. For example, if a functional group such as those mentioned above is attached to the tip of the alkyl group acting as a spacer, the degree of the functional group freedom can be increased and reactivity is improved. Derivatives having a substituted alkyl group to which the above-mentioned functional groups are added or in which the above-mentioned functional groups are substituted with substituents can also be suitably used as intermediates for synthesizing derivatives that can be used for resist compositions or the like. In addition, derivatives having a substituted alkyl group in which the above-mentioned functional groups and substituted groups are protected by a protecting group can also be suitably used as the intermediates.

A calixarene derivative (II) in which two adjacent Zs are bonded to form a substituted or unsubstituted alkylene group having 1 to 8 carbon atoms in the formula (1), that is, the calixarene derivative (II) shown by the formula (13) is another preferred embodiment of the present invention. The conformation can be firmly fixed by such a structure to provide a useful inclusion compound that can hold a specific compound.

[Formula 18]

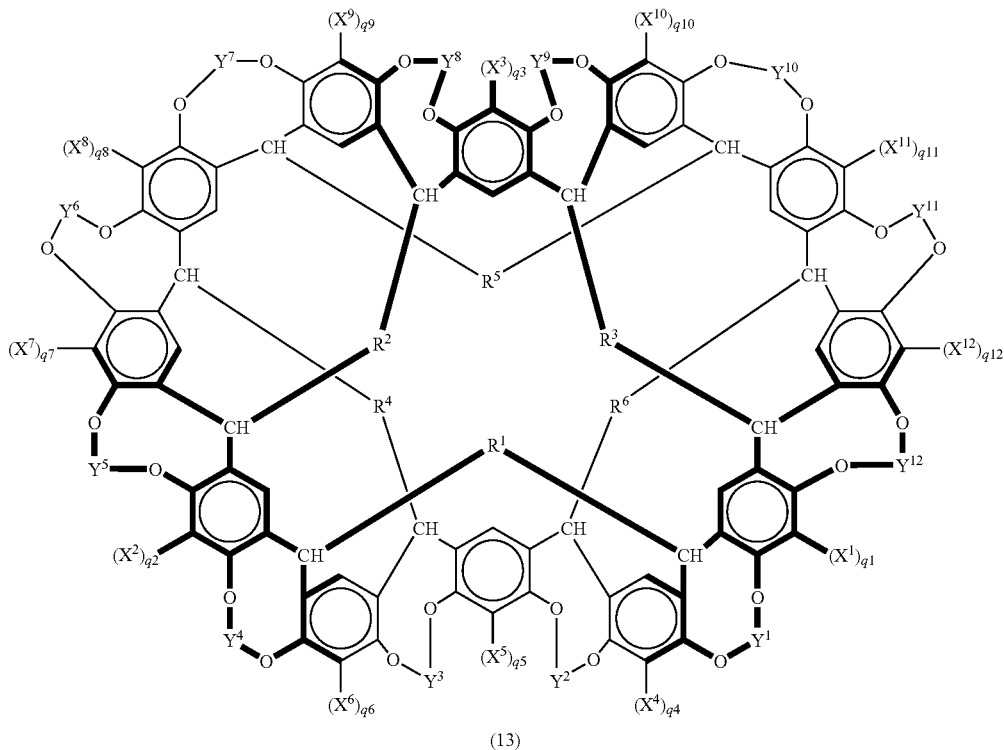

(13)

wherein $R^1$ to $R^6$ individually a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Y^1$ to $Y^{12}$ individually represent a substituted or unsubstituted alkylene group having 1 to 8 carbon atoms; $q^1$ to $q^{12}$ individually represent an integer of 0 or 1.

In the calixarene derivatives (I) and (II), although the substituents ($X^1$ to $X^{12}$) for one aromatic ring may not be present, various substituents may be provided according to the object. As such substituents ($X^1$ to $X^{12}$), a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, and a substituted or unsubstituted phenoxy group can be given.

In the calixarene derivatives (I) and (II), when the aromatic ring is a 1-substituted or unsubstituted resorcinol ring, the aromatic ring portion preferably has the structure shown by the formula (14), wherein X is preferably a hydrogen atom or a methyl group.

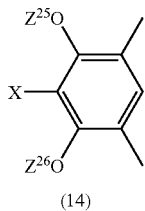

[Formula 19]

(14)

wherein X represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $Z^{25}$ and $Z^{26}$ individually represent a hydrogen atom, a group having a polymerizable functional group, a group having an alkali-soluble group, or a substituted or unsubstituted alkylene group having 1 to 8 carbon atoms.

In the calixarene derivative (I) or (II), $R^1$ to $R^6$ are individually a substituted or unsubstituted alkylene group having 1 to 8 carbon atoms. For easy formation of a basic cyclic structure, particularly preferably $R^1$ to $R^6$ are alkylene groups having 3, 5, 7, or 8 carbon atoms. Moreover, a basic skeleton of a cyclic compound can be obtained at a very high yield when all the $R^1$ to $R^6$ are linear alkylene groups having three carbon atoms.

When the calixarene derivative having a polymerizable functional group is used in a curable composition, it is usually used together with a solvent and a polymerization initiator. As the polymerization initiator, photo initiators and heat initiators such as benzoin, benzoin ethyl ether, dibenzyl, isopropyl benzoin ether, benzophenone, Michiler's ketone chlorothioxanthone, dodecyl thioxanethone, dimethyl thioxanethone, acetophenone diethyl ketal, benzyl dimethyl ketal, and a-hydroxycyclohexyl phenyl ketone can be given. At least one of these initiators is preferably used.

As the solvent, alcohol solvents, ether solvents, halogenated hydrocarbon solvents, aromatic hydrocarbon solvents, amide solvents, and the like can be given.

When the calixarene derivative is used in a photoresist composition, it is usually used together with the same solvent as those mentioned above.

Next, a method for manufacturing the calixarene derivative will be described. First, a calixarene compound shown by the formula (11) which forms a basic skeleton is obtained according to the above-mentioned method.

The hydrogen atom in the phenolic hydroxyl group in the calixarene compound of the formula (11) thus obtained is substituted with a group having a polymerizable functional group, a group having an alkali-soluble group, and/or a substituted alkyl group having an alkyl chain with a 1 to 8 carbon atom content to obtain a calixarene derivative (I). Substitution of the hydrogen atom in the phenolic hydroxyl group is carried out using a conventionally known method.

For example, the calixarene derivative (I) can be obtained by adding a compound having a group which is reactive with the phenolic hydroxyl group such as a halogen atom or an epoxy group and a desirable functional group such as a polymerizable functional group to the calixarene compound of the formula (11) and reacting in a solvent such as THF in the presence of a catalyst such as triethernolamine.

The calixarene derivative (II) can be obtained by reacting a substituted alkane having a group reactive with a phenolic hydroxyl group at the both ends or the like with the calixarene compound of the formula (11).

EXAMPLES

The present invention will now be described in more detail by way of examples, which should not be construed as limiting the present invention.

Example 1

Synthesis of Calixarene Compound (Hereinafter Referred to as "CRA") by the Reaction of Resorcinol and Glutaraldehyde(1,5-pentanedial)

Figure 2:
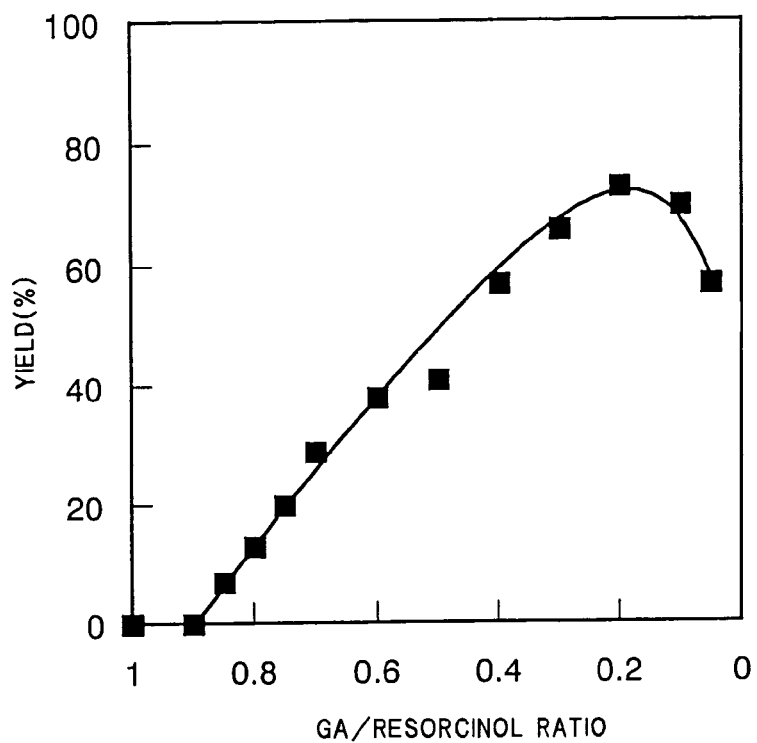
FIG. 2 is a graph showing the relationship between the glutaraldehyde/resorcinol ratio and the yield.

The figure 2.20 g (20 mmol) of resorcinol was added to and dissolved in 4.5 ml of ethanol, and 1.5 ml of hydrochloric acid was added. The solution was cooled with ice to 5° C. while stirring, and 0.40 g (2 mmol) of 50% aqueous solution of glutaraldehyde was slowly dropped. Then, the mixture was heated at 80° C. for 48 hours to obtain a turbid yellow solution. The suspension was poured into methanol. The resulting precipitate was collected by filtration and washed three times with methanol. The solid thus obtained was dried for 24 hours under reduced pressure at room temperature. As a result, a pale yellow powder was obtained. The structure was confirmed by MALDI-TOF-MS, IR, and $^1$H-NMR. The results are shown below, and the structure of the compound is shown by the formula (15). In the formula (15), symbols a to f attached to hydrogen atoms correspond to the hydrogen atom symbols in the NMR data.

MALDI-TOF-MS: Production of only a compound having a molecular weight of 1705.86 was confirmed. Amount: 0.43 g (yield: 79%) IR (film method): (cm$^{-1}$) 3406 ($v_{OH}$); 2931 ($v_{C-H}$); 1621, 1505, 1436 ($v_{C=C(aromatic)}$) $^1$H-NMR (500 MHz, Solvent CDCl$_3$, Internal standard TMS): δ (ppm)=0.86 to 2.35 (b, 32.0H, H$^a$, H$^b$), 3.98 to 4.22(m, 4.0H, H$^C$), 6.09 to 7.42 (m, 8.0H, aromaticH$^d$, H$^e$), 8.65 to 9.56 (m, 8.0H; OH$^f$)

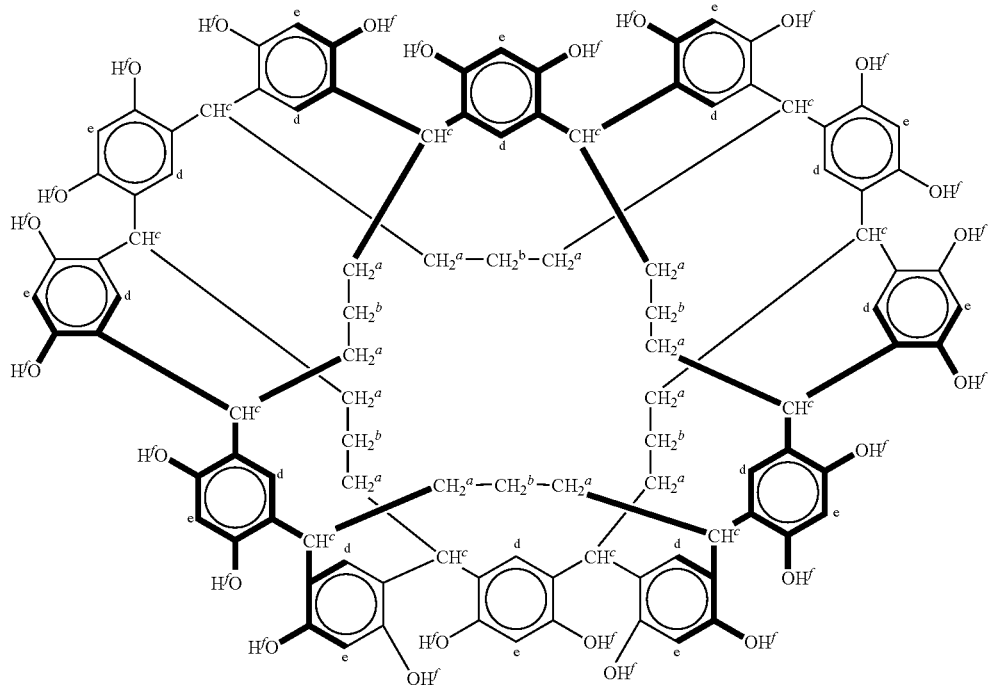

(15)

Example 2

Study on Glutaraldehyde/Resorcinol Ratio

A cyclic CRA compound was synthesized in the same manner as in Example 1 except that 9 ml of N-methylpyrrolidone (NMP) was used as a solvent, 3.0 ml of hydrochloric acid was added, 20 mmol of resorcinol was used, and various amounts of glutaraldehyde (GA) was used. The results are shown in FIG. 2. The yield of the cyclic compound was confirmed to increase as the amount of GA decreases. The yield was maximum (73%) when the charge ratio was 0.2 (GA:resorcinol=1:5). When the charge ratio was 1.0 (GA:resorcinol=1:1), the product was gelatinized 10 minutes after the start of reaction.

Example 3

Study on Reaction Time

Figure 3:
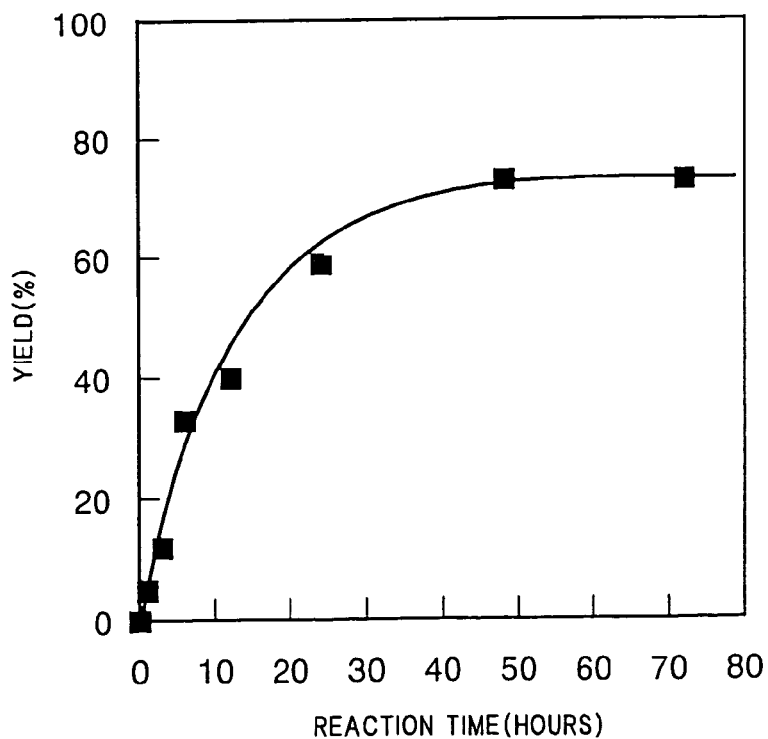
FIG. 3 is a graph showing the relationship between the reaction time and the yield.

A cyclic CRA compound was synthesized in the same manner as in Example 2 except that the GA:resorcinol mol ratio was 0.2 and the reaction time was variously changed. The results are shown in FIG. 3. The yield of the cyclic compound was confirmed to increase as the reaction time increases. The maximum yield of 73% was attained 48 hours after the start of reaction.

Example 4

Study on Monomer Concentration

Figure 4:
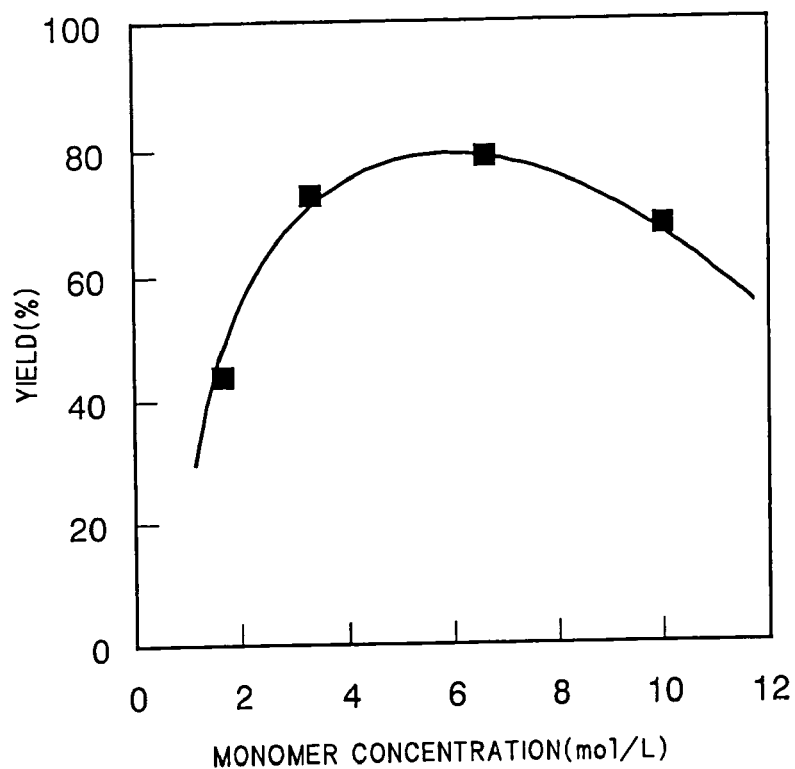
FIG. 4 is a graph showing the relationship between the monomer concentration and the yield.

A cyclic CRA compound was synthesized in the same manner as in Example 3 except that the initial monomer concentration (the total concentration of glutaraldehyde and resorcinol) in the reaction solution was variously changed. The results are shown in FIG. 4. The yield was confirmed to increase as the monomer concentration increases up to the monomer concentration of 6.6 mol/l, at which the yield was maximum. The yield decreased at higher monomer concentrations.

As a result of the study of these conditions, optimum conditions were confirmed to be the charge ratio of 0.2, the monomer concentration of 6.6 mol/l, and the reaction time of 48 hours.

Example 5

Determination of Reaction Intermediate

Figure 10:
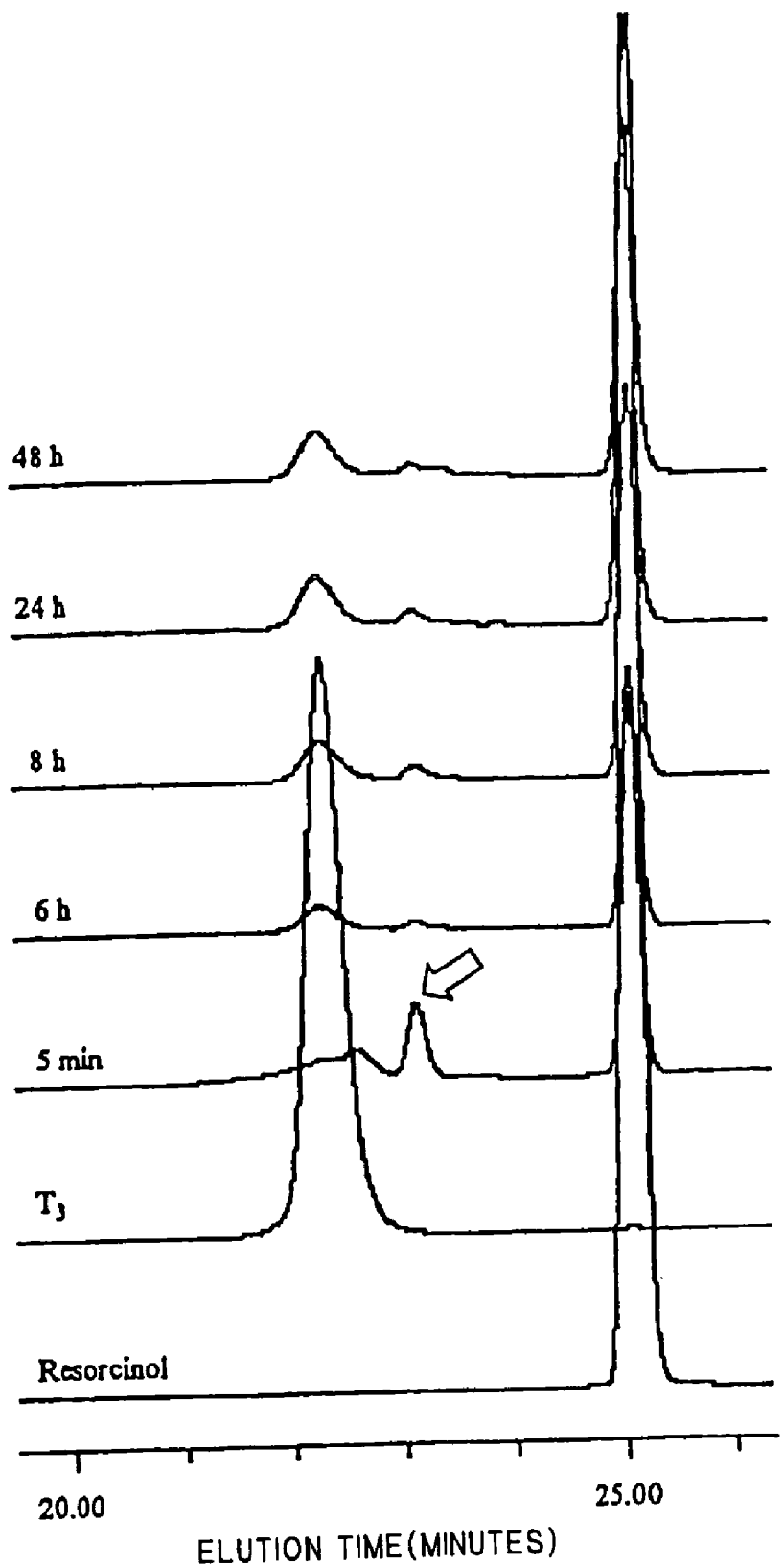
FIG. 10 is a chromatogram showing the result of chromatography disregarding the size in Example 5.

To clarify the reaction mechanism, the following experiment was performed. The reaction between 22 g (0.2 mol) of resorcinol and 8 g (0.02 mmol) of 50% aqueous solution of glutaraldehyde was performed using 15 ml hydrochloric acid as a catalyst in the 45 ml (4.8 mol/l) ethanol at 80° C. After a lapse of 5 minutes, 6 hours, 8 hours, 24 hours and 48 hours, the reacted solutions were analyzed using chromatography disregarding the size. A change of properties with time was identified. The obtained chromatogram is shown in FIG. 10. As shown in FIG. 10, it is cleared that 5 minutes after the start of reaction major intermediate compound was identified and then, with decreasing of the intermediate compound, CRA cyclic compound ($T_3$ in FIG. 10) was produced.

Next, a reaction in the same manner as described above was performed. After two hours from the start of reaction, a reacted solution was removed and soluble portion and insoluble portion were separated from each other. A methanol soluble portion was separated into fraction 1 (Rf value: 0.61) and fraction 2 (Rf value: 0.82) by using silica gel column chromatography (developer: ethyl acetate) under reduced pressure in which methanol was removed. A component contained in fraction 1 was identified to be a raw material resorcinol by $^1$H-NMR. The structure of a component contained in fraction 2 was confirmed by MALDI-TOF-MS, IR, $^1$H-NMR and $^{13}$C-NMR. As a result, it is identified that the intermediate compound 1 shown in FIG. 1 was produced by reaction of one molecule of glutaraldehyde and four molecule of resorcinol. Result of analysis is described below.

Result of Analysis of Fraction 2

IR (KBr method): (cm$^{-1}$) 3291 ($v_{OH}$); 2935 ($v_{C-H}$); 2863 ($v_{C-H}$); 1617, 1508, 1457 ($v_{C=C(aromatic)}$) $^1$H-NMR (500 MHz, Solvent DMSO-ds, Internal standard TMS): δ (ppm)= 1.09(quinted, J=7.50 Hz, 2.0H), 1.78(quinted, J=7.50 Hz, 4.0H), 4.27(t, J=7.50 Hz, 2.0H), 6.09 to 6.12 (m, 4.0H) 6.21 (d, J=8.50 Hz, 4.0H), 6.74(d, J=8.50 Hz, 4.0H), 8.84 to 8.87 (m, 8.0H), $^{13}$C-NMR (125 MHz, Solvent DMSO-ds, Internal standard TMS): δ(ppm)=26.7, 34.4, 39.0, 102.6, 106.0, 122.6, 128.5, 155.4, 155.8 Mass-spectrometry MALDI-TOF-MS Calculated value (m/z): 504.8 [M+H]$^+$ Found value (m/z): 504.9 [M+H]$^+$.

Next, separated 0.10 g (0.2 mmol) intermediate compound 1 was dissolved in 4.5 ml of ethanol, 1.5 ml of hydrochloric acid was added thereto, and then reaction was caused at 80° C. for 48 hours. After reaction was completed, the reacted solution was poured into methanol and separated into methanol soluble portion and insoluble portion. The methanol insoluble portion was further cleansed by using methanol and then dried. A structure of the obtained pale yellow solid was identified by MALDI-TOF-MS, IR, and $^1$H-NMR. As a result, the solid was confirmed to be CRA cyclic compounds shown in the formula (15). On the other hand, by separating the methanol soluble portion using silica gel column chromatography (developer: ethyl acetate) 0.049 g of resorcinol was obtained from fraction 1 (Rf value: 0.61). The yield of resorcinol calculated from the following calculation was 91%.

Yield of resorcinol=obtained resorcinol(mol)/(resorcinol(mol) composing used intermediate compound 1−resorcinol(mol) composing obtained CRA cyclic compound)

As a result mentioned above, the CRA cyclic compounds were confirmed to be produced from intermediate compound 1 without addition of dial under acid state condition. As production mechanism of CRA cyclic compounds, it was proved that as shown in FIG. 1 firstly an intermediate compound is obtained, and then with a removal of resorcinol, reaction goes on to produce the CRA cyclic compounds.

Example 6
Synthesis of CRA from 1,7-heptanedial and Resorcinol 2.20 g (20 mmol) of resorcinol was added to and dissolved in 4.5 ml of ethanol, and 1.5 ml of hydrochloric acid was added. The solution was cooled with ice to 5° C. while stirring, and 0.26 g (2 mmol) of 1,7-heptanedial was slowly dropped. The mixture was heated at 80° C. for 48 hours to obtain a turbid yellow solution. The suspension was poured into methanol. The resulting precipitate was collected by filtration and washed three times with methanol. The solid thus obtained was dried for 24 hours under reduced pressure at room temperature. As a result, a pale yellow solid was obtained. The structure was confirmed by MALDI-TOF-MS, IR, and $^1$H-NMR. The results are shown below, and the structure of the component is shown by the formula (16). In the formula (16), symbols a to f attached to hydrogen atoms correspond to the hydrogen atom symbols in the NMR data.

Amount: 0.12 g (yield: 20%) IR (film method): (cm$^{-1}$) 3406 ($v_{OH}$); 2931 ($v_{C-H}$); 1621, 1505, 1436 ($v_{C=C(aromatic)}$) $^1$H-NMR (500 MHz, Solvent CDCl$_3$, Internal standard TMS): δ (ppm)=0.85 to 2.35 (b, 20.0H, H$^a$, H$^b$), 3.98 to 4.22 (m, 4.0H, H$^c$), 6.09 to 7.42 (m, 8.0H, aromaticH$^d$, H$^e$), 8.65 to 9.56 (m, 8.0H, OH$^f$) Mass-spectrometry MALDI-TOF-MS Calculated value (m/z): 1884.9 [M+H]$^+$ Found value (m/z): 1885.3 [M+H]$^+$.

[Formula 21]

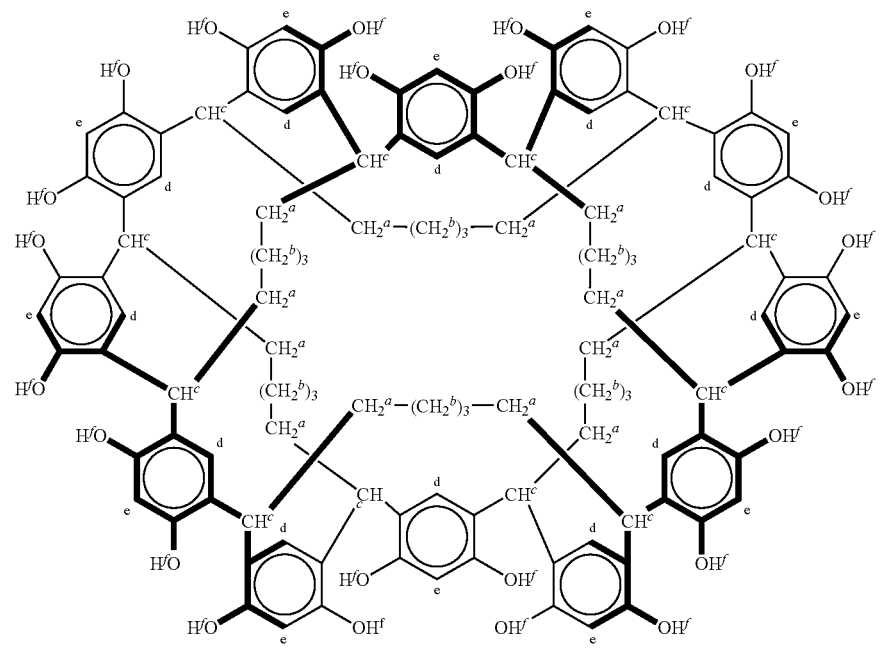

(16)

Example 7

Synthesis of CRA from 1,9-nonanedial and Resorcinol

CRA was synthesized, and the structure was confirmed in the same manner as in Example 6 except for using 0.31 g (2 mmol) of 1,9-nonanedial instead of 1,7-heptanedial. The structure of the compound is shown in the formula (17). In the formula (17), symbols a to f attached to hydrogen atoms correspond to the hydrogen atom symbols in the NMR data.

Amount: 0.085 g (yield: 25%) IR (film method): (cm$^{-1}$) 3406 ($\nu_{OH}$); 2931 ($\nu_{C-H}$); 1621, 1505, 1436 ($\nu_{C=C(aromatic)}$) $^1$H-NMR (500 MHz, Solvent CDCl$_3$, Internal standard TMS): δ (ppm)=0.84 to 2.38 (b, 28.0H, H$^a$, H$^b$), 3.98 to 4.22 (m, 4.0H, H$^c$), 6.09 to 7.42 (m, 8.0H, aromaticH$^d$,H$^e$), 8.65 to 9.56 (m, 8.0H, OH$^f$) Mass-spectrometry MALDI-TOF-MS Calculated value (m/z): 2075.06 [M+Na]$^+$ Found value (m/z): 2074.14 [M+Na]$^+$.

[Formula 22]

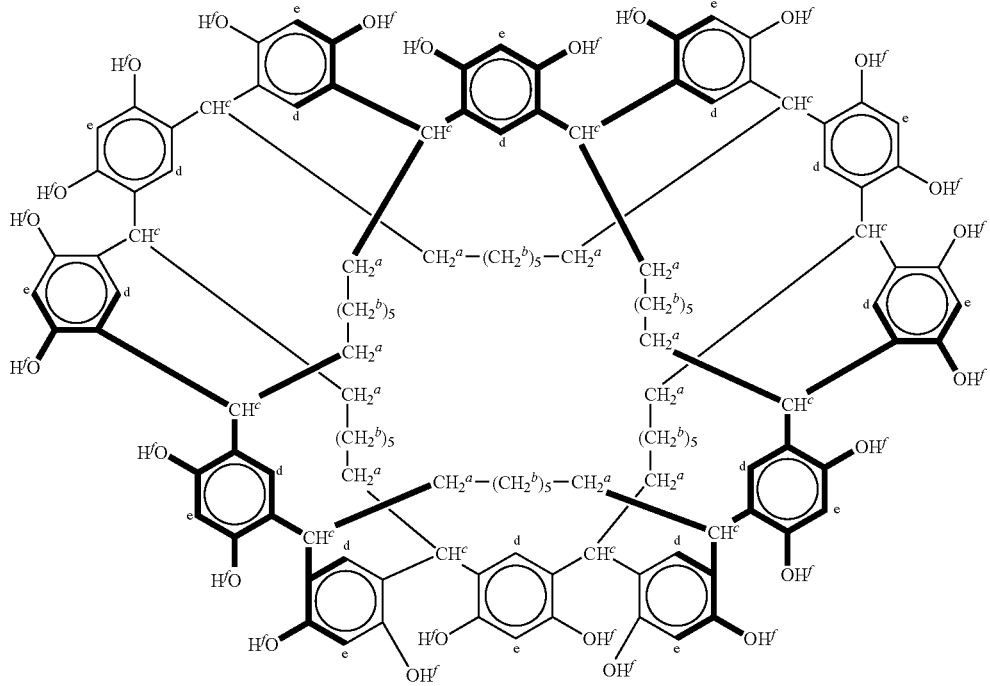

(17)

Example 8

Synthesis of CRA from 1,10-decanedial and Resorcinol

CRA was synthesized, and the structure was confirmed in the same manner as in Example 6 except for using 0.34 g (2 mmol) of 1,10-decanedial instead of 1,7-heptanedial. The structure of the compound is shown in the formula (18). In the formula (18), symbols a to f attached to hydrogen atoms correspond to the hydrogen atom symbols in the NMR data.

Amount: 0.042 g (yield: 6%) IR (film method): (cm$^{-1}$) 3406 ($v_{OH}$); 2931 ($v_{C-H}$); 1621, 1505, 1436 ($v_{C=C(aromatic)}$) $^1$H-NMR (500 MHz, Solvent CDCl$_3$, Internal standard TMS): δ (ppm)=0.80 to 2.33. (b, 32.0H, H$^a$, H$^b$), 3.98 to 4.22 (m, 4.0H, H$^c$), 6.09 to 7.42 (m, 8.0H, aromaticH$^d$, H$^e$), 8.65 to 9.56 (m, 8.0H, OH$^f$) Mass spectrometry MALDI-TOF-MS Calculated value (m/z): 1440.76 [M+Na]$^+$ Found value (m/z): 1440.70 [M+Na]$^+$.

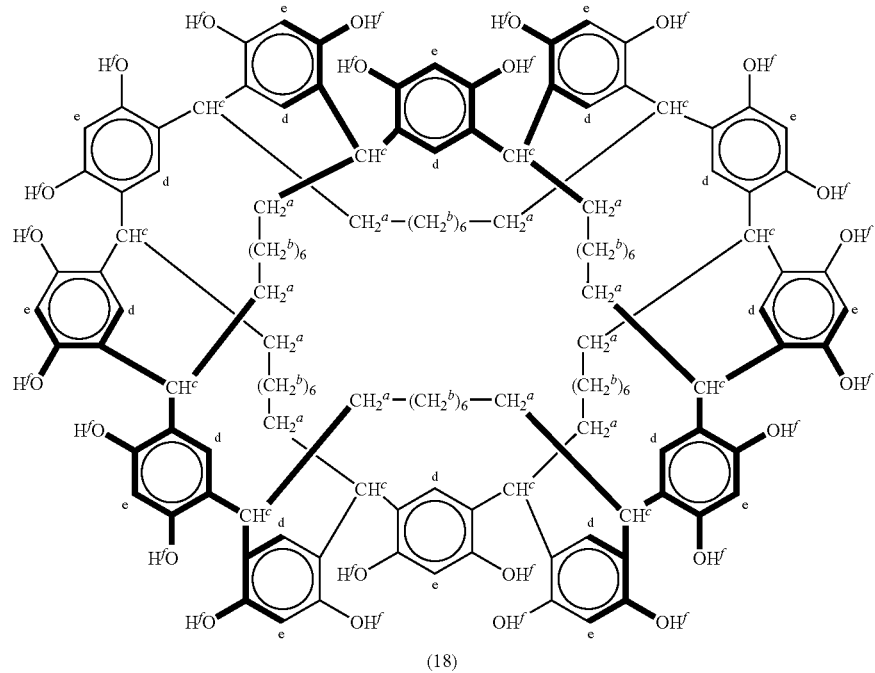

[Formula 23]

(18)

Example 9

Synthesis of CRA from Methyl Resorcinol and Glutaraldehyde 22.0 g (0.2 mol) of resorcinol was added to and dissolved in 45 ml of ethanol, and 15 ml of hydrochloric acid was added. The solution was cooled with ice to 5° C. while stirring, and 4.0 g (0.02 mol) of 50% aqueous solution of glutaraldehyde was slowly dropped. The mixture was heated at 80° C. for 48 hours to obtain a turbid yellow solution. The suspension was poured into methanol. The resulting precipitate was collected by filtration and washed three times with methanol. The solid thus obtained was dried for 24 hours under reduced pressure at room temperature. As a result, a pale yellow powder was obtained. The structure was confirmed by MALDI-TOF-MS, IR, and $^1$H-NMR. The results are shown below, and the structure of the component is shown by the formula (19). In the formula (19), symbols a to f attached to hydrogen atoms correspond to the hydrogen atom symbols in the NMR data.

Amount: 0.81 g (yield: 13%) IR (film method): (cm$^{-1}$) 3406 ($v_{OH}$); 2931 ($v_{C-H}$); 1621, 1505, 1436 ($v_{C=C(aromatic)}$) $^1$H-NMR (500 MHz, Solvent CDCl$_3$, Internal standard TMS): δ (ppm)=0.96 to 1.97 (m, 24.0H, H$^a$, H$^b$, H$^e$), 4.00 to 4.41 (m, 4.0H, H$^c$), 6.21 to 7.24 (m, 4.0H, H$^d$), 8.10 to 9.10 (m, 8.0H, H$^f$) Mass spectrometry MALDI-TOF-MS Calculated value (m/z): 1894.84 [M+Na]$^+$ Found value (m/z): 1894.53 [M+Na]$^+$.

[Formula 24]

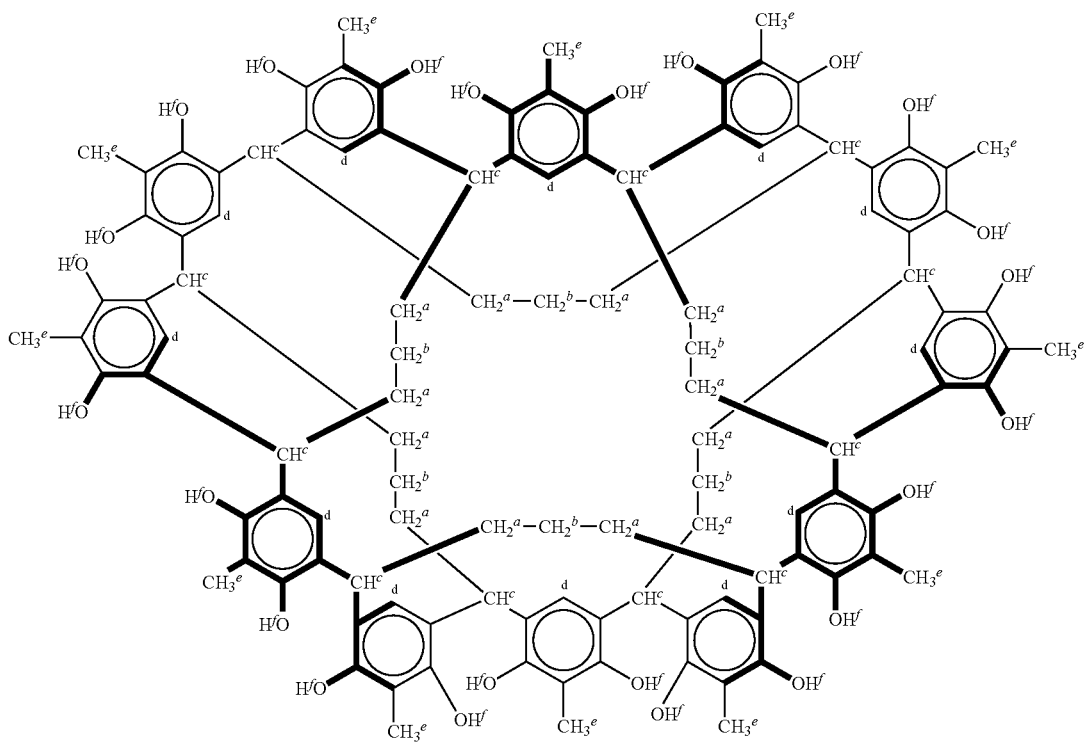

(19)

By $^1$H—$^1$H COSY spectrum of the compound obtained in Example 9, coupling of protons in benzene rings was confirmed, indicating that the CRA rings are in close proximity. The results also supported that the obtained compound was a cyclic compound.

Example 10

Synthesis of Derivative Using Methacrylic Acid Chloride (MAC) (Introduction of Radically Polymerizable Functional Group)

3.00 g (1.76 mmol, OH equivalent: 42.2 mmol) of CRA (hereinafter referred to as $T_3$) obtained in the same manner as in Example 1 was suspended in 21.2 ml (152 mmol) of triethylamine. After the addition of 30 ml of anhydrous THF, the mixture was cooled with ice. Then, 13.30 g (127 mmol) of methacrylic acid chloride (MAC) was dropped in a nitrogen atmosphere, and the resulting mixture was stirred at room temperature for 24 hours. After the reaction, the reaction mixture was diluted with ethyl acetate, washed with an aqueous solution of sodium hydrogencarbonate, then three times with distilled water, and dried over anhydrous magnesium sulfate. Then, reprecipitation was carried out two times using ethyl acetate as a good solvent and ether as a poor solvent to obtain a milky white powdery solid. The filtrate was concentrated, and methanol was added to collect deposited white solid. The structure of the resulting solid was determined by IR and $^1$H-NMR. The results are shown below, and the structure of the component is shown by the formula (20). In the formula (20), symbols a to g attached to hydrogen atoms correspond to the hydrogen atom symbols in the NMR data. The results confirmed that the esterification rate of the derivative obtained was 100%. The compound shown in the formula (20) is hereinafter referred to as $T_3$-1.

Amount: 2.56 g (44%) IR(KRS): (cm$^{-1}$) 2929 ($v_{CH}$); 1739 ($v_{C=O(ester)}$); 1637 ($v_{C=C(methacryl)}$); 1494 ($v_{C=C(aromatic)}$); 1294, 1131 ($v_{C—O—C}$) $^1$H-NMR (500 MHz, Solvent DMSO, Internal standard TMS): δ (ppm)=1.64 to 2.36 (m, 36.0H, H$^a$, H$^b$, H$^f$), 3.80 to 4.45 (m, 4.00H, H$^c$), 5.60 to 6.25 (m, 16.1H, H$^g$, H$^{g'}$), 6.60 to 7.50 (m, 8.00H, H$^e$, H$^d$)

[Formula 25]

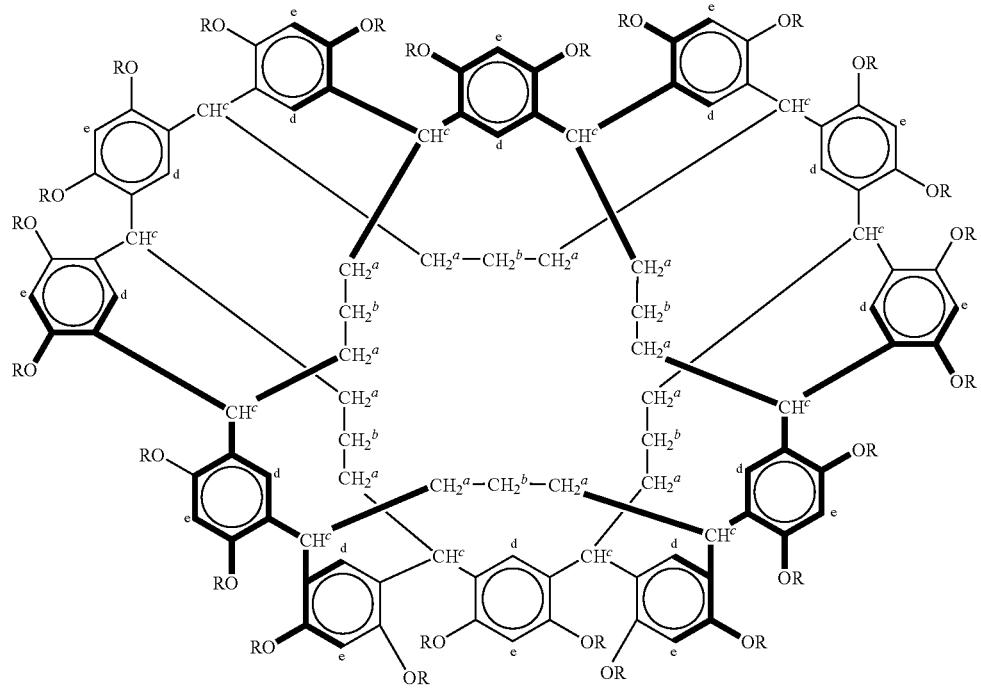

(20)

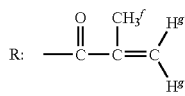

Example 11

Synthesis of Derivative Using Glycidyl Methacrylate (GMA) (Introduction of Radically Polymerizable Functional Group)

0.50 g (0.29 mmol, OH equivalent: 7.03 mmol) of $T_3$ was weighed and 0.22 g (0.030 mmol) of tetrabutyl ammonium bromide (hereinafter referred to as TBAB), 5 ml of NMP was added. Then, after the addition of 2.00 g (0.59 mmol) of glycidyl methacrylate (GMA), the resulting mixture was stirred at 100° C. for 48 hours. After the reaction, the reaction mixture was diluted with ethyl acetate, washed with a hydrochloric acid aqueous solution, then three times with distilled water, and dried over anhydrous magnesium sulfate. Then, reprecipitation was carried out using ethyl acetate as a good solvent and cyclohexane as a poor solvent to obtain a pale yellow powdery solid. The structure of the resulting solid was determined by IR and $^1$H-NMR. The results are shown below, and the structure of the component is shown by the formula (21). In the formula (21), symbols a to k attached to hydrogen atoms correspond to the hydrogen atom symbols in the NMR data. The results confirmed that the etherification rate of the derivative obtained was 100%. The compound shown in the formula (21) is hereinafter referred to as $T_3$-2.

Amount: 1.38 g (92%) IR(KRS): (cm$^{-1}$): 3438 ($v_{OH}$); 2931 ($v_{CH}$); 1714 ($v_{C=O(ester)}$); 1634 ($v_{C=C(methacryl)}$); 1502 ($v_{C=C(aromatic)}$); 1296, 1172($v_{C-O-C}$) $^1$H-NMR (500 MHz, Solvent DMSO, Internal standard TMS): δ (ppm)=1.83 to 2.17 (m, 36.0H, H$^a$, H$^b$, H$^j$), 3.58 to 5.60 (m, 52.0H, H$^c$, H$^f$, H$^g$, H$^h$, H$^i$), 5.69 to 6.02 (m, 16. OH, H$^k$, H$^{k'}$), 6.39 to 7.70 (m, 8.00H, H$^e$, H$^d$)

[Formula 26]

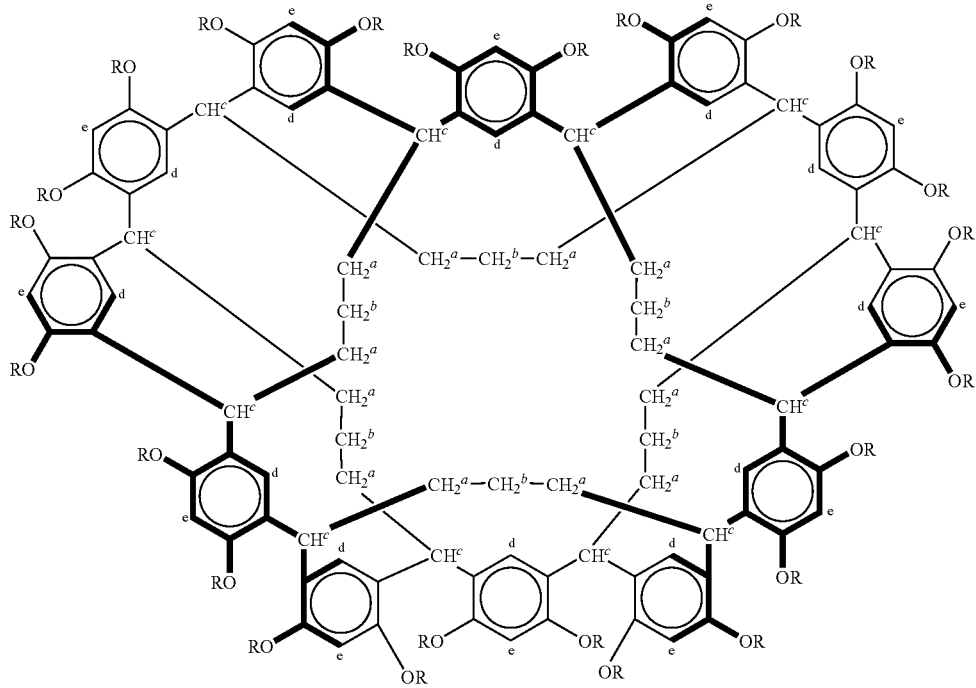

(21)

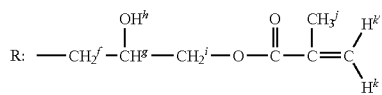

Examples 12-15

Study on Synthesis Conditions of $T_3$-2

The derivative was synthesized in the same manner as in Example 11 except that the charged amount of GMA and the temperature were changed as shown in Table 1. The yield and etherification rate (measured by $^1$H-NMR) are shown in Table 1.

TABLE 1

| GMA mmol(OHeq.) | Temperature (° C.) | Etherification rate (%) | Yield (%) |
|---|---|---|---|
| 0.29(1.0) | 70 | 65 | 45 |
| 0.29(1.0) | 100 | 91 | 55 |
| 0.44(1.5) | 100 | 98 | 77 |
| 0.59(2.0) | 100 | 100 | 92 |

TBAB: 5 mol %

Examples 16 and 17

Photocure Reaction of $T_3$-1 and $T_3$-2

Figure 5:
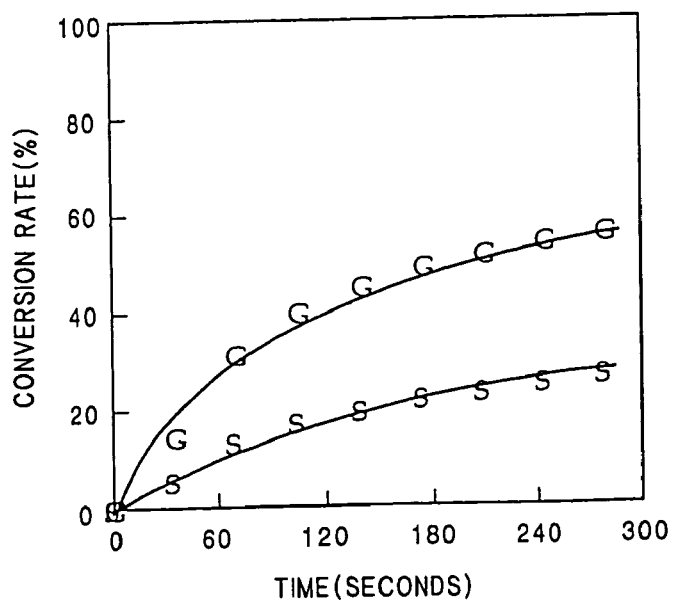
FIG. 5 is a graph showing the change in the conversion rate due to photocure reactions in Examples 16 and 17.

In Example 16, 3 parts by weight of an initiator shown by the formula (22) (Irgacure 907 manufactured by Ciba Geigy) and 1 part by weight of 2-ethyl anthraquinone were added to 100 parts by weight of $T_3$-1. After the addition of a small amount of THF, the resulting composition was applied to a KBr plate. The coating was dried at room temperature and irradiated with light at 250 W, luminosity 8 mW/cm$^2$ (254 nm) to effect a photocure reaction. The conversion rate was calculated from the attenuation of absorption originating from the methacryloyl group ($v_{C=C}$) at 1638 cm$^{-1}$ in the FT-IR. The same experiment was conducted as Example 17 using $T_3$-2. The results are shown in FIG. 5. In FIG. 5, G indicates the conversion rate of $T_3$-2, and S indicates the conversion rate of $T_3$-1.

[Formula 27]

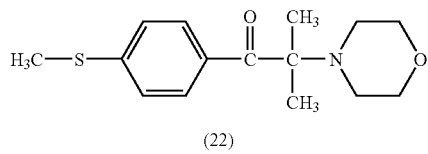

(22)

Cross-linking that results in curing was confirmed to have occurred both in $T_3$-1 and $T_3$-2. In addition, from the fact that the conversion rates of $T_3$-1 and $T_3$-2 are respectively 56% and 25% in spite of their possession of 24 methacryloyl groups, $T_3$-2 was confirmed to have significantly high photo reactivity. This is considered to be due to a longer molecular chain of the functional group that allows a higher degree of freedom and efficiently accelerates cross-linking. In addition, hydroxyl groups present near the methacryloyl groups of $T_3$-2 are thought to have contributed to the efficient radical polymerization.

Example 18

Introduction of Alkali-Soluble Groups into $T_3$-2

0.30 g (0.175 mmol, OH equivalent: 4.22 mmol) of $T_3$-2 was dissolved in 5 ml of N-methylpyrrolidone (NMP). After the addition of 0.67 ml (4.22 mmol) of triethylamine and a solution of 0.64 g (4.22 mmol) of cis-1,2,3,6-tetrahydrophthalic acid anhydride (THPA) in 1 ml of NMP, the mixture was stirred for 24 hours while heating at 70° C. After the reaction, the reaction mixture was dropped to 0.05N hydrochloric acid aqueous solution. The insoluble portion was dried under reduced pressure. The dried product was dissolved in chloroform, followed by pump-up. As a result, a pale yellow powdery solid was obtained. The structure of the resulting solid was determined by IR, $^1$H-NMR, and MALDI-TOF-MS. The results are shown below, and the structure of the component is shown by the formula (23). In the formula (23), symbols a to p attached to hydrogen atoms correspond to the hydrogen atom symbols in the NMR data. The results confirmed that the esterification rate of the derivative obtained was 100%. The compound shown in the formula (23) is hereinafter referred to as $T_3$-2a.

Amount: 0.495 g (96%) IR(KRS): (cm$^{-1}$): 3515 ($v_{OH}$); 1724 ($v_{C=O(ester)}$); 1633 ($v_{C=C(methacryl)}$); 1503 ($v_{C=C(aromatic)}$); 1294, 1183 ($v_{C-O-C}$)

$^1$H-NMR (500 MHz, Solvent DMSO, Internal standard TMS): δ (ppm)=1.43 to 2.34 (m, 68.0H, H$^a$, H$^b$, H$^i$, H$^l$, H$^n$), 2.51 to 3.20 (m, 16.0H, H$^k$, H$^o$), 3.62 to 5.02 (m, 36.0H, H$^c$, H$^f$, H$^h$), 5.00 to 6.35 (m, 40.0H, H$^g$, H$^j$, H$^i$, H$^m$, H$^{m'}$), 6.39 to 7.70 (m, 8.00H, H$^e$, H$^d$), 11.8 to 12.5 (m, 4.58H, H$^p$) Mass-spectrometry (MALDI-TOF-MS) Calculated value (m/z): 8769.20[M+H$^+$] Found value (m/z): 8770.95[M+H$^+$].

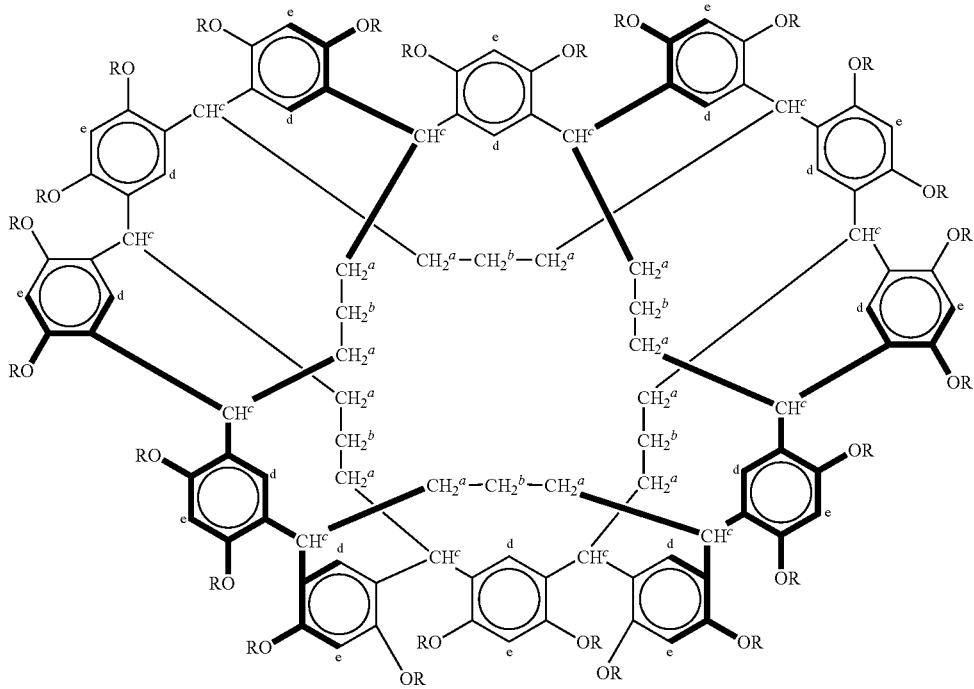

(23)

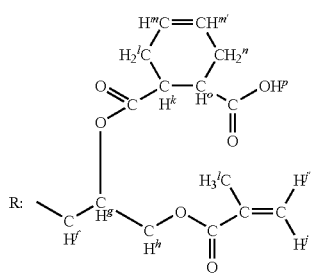

Example 19

Synthesis of Derivative Using 3-chloro-1-propanol (Introduction of Spacer)

0.30 g (0.18 mmol, OH equivalent: 4.22 mmol) of $T_3$ and 0.07 g (0.21 mmol) of TBAB were weighed and dissolved in 3 ml of NMP. Then, after the addition of 0.586 g (4.22 mmol) of potassium carbonate, the mixture was stirred at 60° C. for 12 hours. After salt formation, 0.35 ml (4.22 mmol) of 3-chloro-1-propanol was dropped, and the mixture was stirred for five hours at 80° C. After the reaction, the reaction mixture was added to a 0.01N hydrochloric acid aqueous solution. The precipitate was dried at 60° C. under reduced pressure and reprecipitated using metanol as a good solvent and ether as a poor solvent to obtain a pale reddish powdery solid. The structure of the resulting solid was determined by IR and $^1$H-NMR. The results are shown below, and the structure of the compound is shown by the formula (24). In the formula (24), symbols a to h attached to hydrogen atoms correspond to the hydrogen atom symbols in the NMR data. The results confirmed that the etherification rate of the solid obtained was 52%. The compound shown in the formula (24) is hereinafter referred to as $T_3$-$3_1$.

Amount: 0.347 g (64%) IR(KRS): (cm$^{-1}$): 3332 ($\nu_{OH}$), 2917 ($\nu_{CH}$), 1613, 1504 ($\nu_{C=C(aromatic)}$), 1286, 1054 ($\nu_{C-O-C}$) $^1$H-NMR (500 MHz, Solvent DMSO-d$_6$, Internal standard TMS); δ (ppm)=1.21 to 2.33 (m, 20.3H, H$^a$ H$^b$, H$^g$), 3.56 to 4.95 (m, 20.6H, H$^c$, H$^f$, H$^h$), 5.79 to 7.81 (m, 8.00H, H$^e$, H$^d$), 7.85 to 9.38 (m, 3.84, H$^j$)

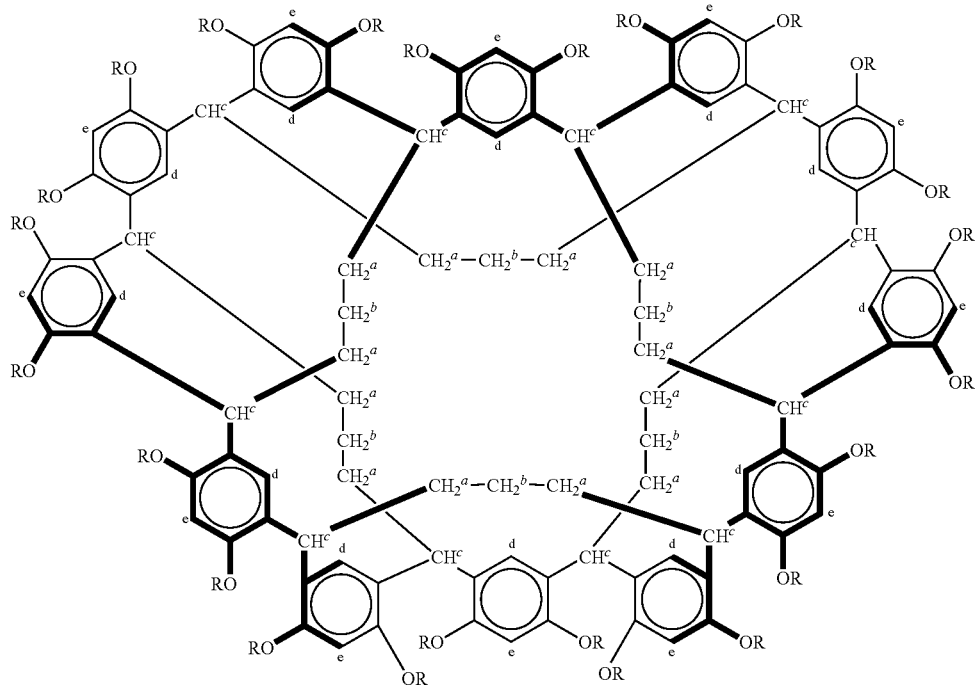

(24)

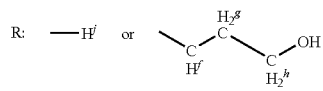

Example 20

Synthesis of Derivative Using 6-chloro-1-hexanol (Introduction of Spacer)

A pale reddish powdery solid was obtained in the same manner as in Example 10, except for using 0.56 ml (4.22 mmol) of 6-chloro-1-hexanol instead of 3-chloro-1-propanol. The structure of the resulting solid was determined by IR and $^1$H-NMR. The results are shown below, and the structure is shown by the formula (25). In the formula (25), symbols a to j attached to hydrogen atoms correspond to the hydrogen atom symbols in the NMR data. The results confirmed that the etherification rate of the derivative obtained was 52%. The compound shown in the formula (25) is hereinafter referred to as $T_3$-$4_1$.

Amount: 0.492 g (68%) IR(KRS): (cm$^{-1}$) 3374 ($\nu_{OH}$), 2935 ($\nu_{CH}$), 1612, 1496 ($\nu_{C=C(aromatic)}$), 1291, 1055 ($\nu_{C-O-C}$) $^1$H-NMR (600 MHz, Solvent DMSO-d$_6$, Internal standard TMS); δ (ppm)=1.31 to 2.41 (m, 45.3H, H$^a$, H$^b$, H$^g$, H$^h$, H$^i$), 3.20 to 4.84 (m, 20.7H, H$^c$, H$^f$, H$^j$), 6.06 to 7.64 (t, 8.00H, H$^e$, H$^d$), 7.70 to 9.10 (m, 3.84H, H$^j$)

[Formula 30]

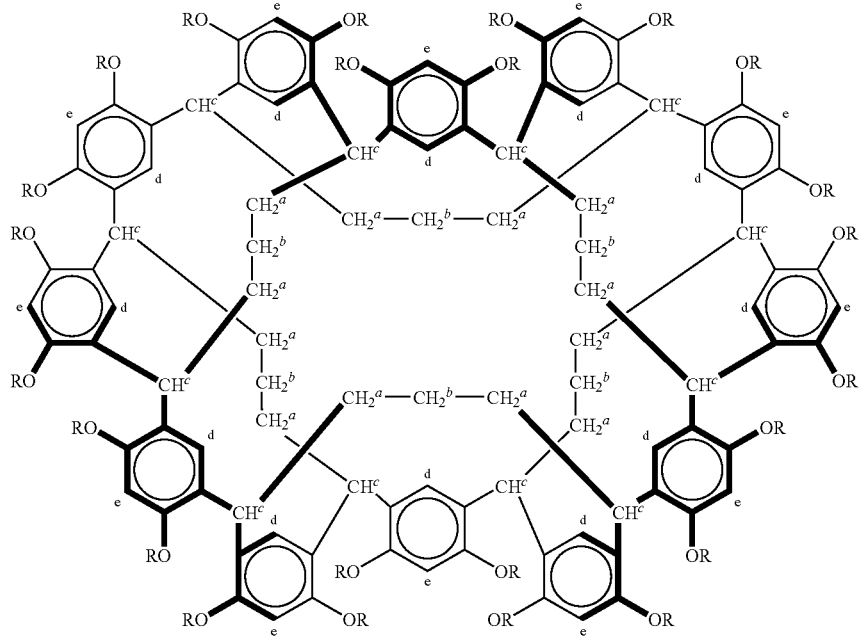

(25)

R: —H$^j$ or 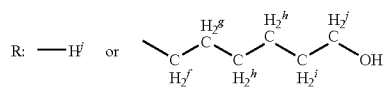

Example 21

Synthesis of Derivative Using 3-chloro-1-propanol (2)

A white solid was obtained in the same manner as in Example 10 except for using 1.65 g (5.06 mmol) of cesium carbonate instead of potassium carbonate, using 0.70 ml (8.44 mmol) of 3-chloro-1-propanol, and reacting the mixture for 24 hours. The structure of the resulting solid was determined by IR and $^1$H-NMR. The results are shown below, and the structure is shown by the formula (26). In the formula (26), symbols a to h attached to hydrogen atoms correspond to the hydrogen atom symbols in the NMR data. The results confirmed that the etherification rate of the solid obtained was 100%. The compound shown in the formula (26) is hereinafter referred to as T$_3$-3.

Amount: 0.04 g (6%) IR(KRS): (cm$^{-1}$): 3391 ($v_{OH}$), 2937 ($v_{CH}$), 1608, 1502 ($v_{C=C(aromatic)}$), 1263, 1053 ($v_{C-O-C}$)

$^1$H-NMR (500 MHz, Solvent DMSO-d$_6$, Internal standard TMS): δ (ppm)=1.25 to 1.51 (m, 4.00H, H$^b$), 1.88 to 2.34 (m, 24.0H, H$^a$, H$^g$), 3.56 to 3.95 (m, 16.0H, H$^h$), 3.72 to 4.35 (m, 4.00H, H$^c$), 4.54 to 4.75 (m, 16.0H, H$^i$), 6.60 to 6.73 (m, 8.00H, H$^e$, H$^d$)

[Formula 31]

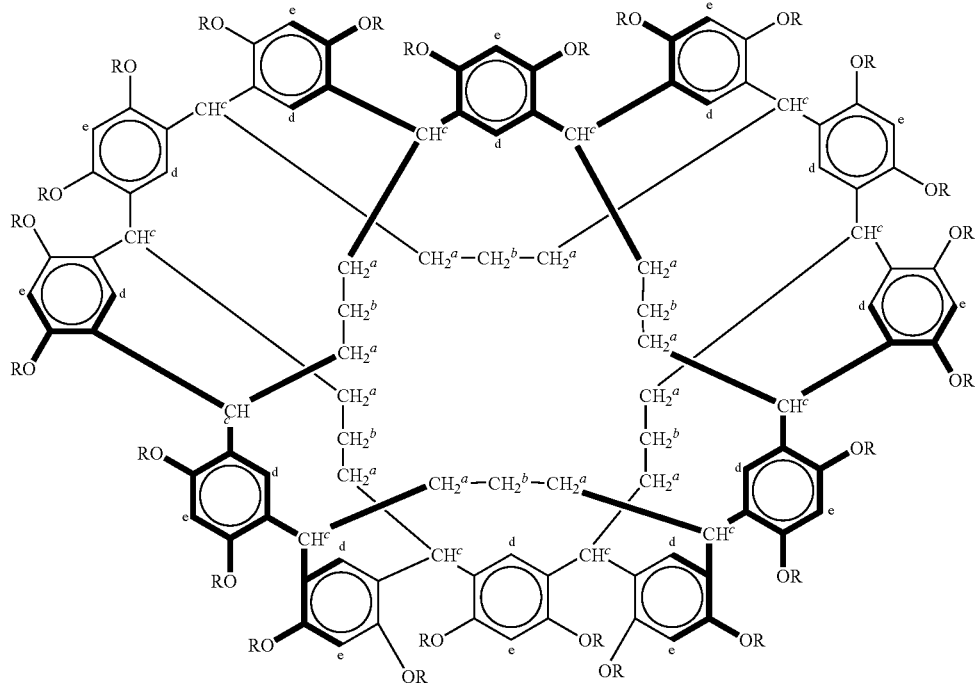

(26)

R: 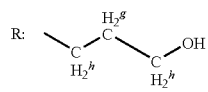

Example 22

Synthesis of Derivative Using 6-chloro-1-hexanol (2)

A brown powdery solid was obtained in the same manner as in Example 11 except for using 1.65 g (5.06 mmol) of cesium carbonate instead of potassium carbonate, using 1.12 ml (8.44 mmol) of 6-chloro-1-hexanol, and reacting the mixture for three days. The structure of the resulting solid was determined by IR and $^1$H-NMR. The results are shown below, and the structure of the compound is shown by the formula (27). In the formula (27), symbols a to j attached to hydrogen atoms correspond to the hydrogen atom symbols in the NMR data. The results confirmed that the etherification rate of the derivative obtained was 100%. The compound shown in the formula (27) is hereinafter indicated as to as $T_3$-4.

Amount: 0.19 g (27%) IR(KRS): (cm$^{-1}$): 3375 ($v_{OH}$), 2935 ($v_{CH}$), 1609, 1500 ($v_{C=C(aromatic)}$) 1264, 1055 ($v_{C-O-C}$) $^1$H-NMR (500 MHz, Solvent DMSO-d$_6$, Internal standard TMS); δ (ppm)=1.31 to 1.82 (m, 78.0H, H$^a$, H$^b$ H$^g$, H$^h$, H$^i$), 3.56 to 3.64 (t, 16.0H, H$^j$), 3.67 to 3.79 (t, 16.0H, H$^f$), 4.02 to 4.11 (m, 4.00H, H$^c$), 5.92 to 6.73 (m, 8.00H, H$^e$, H$^d$)

[Formula 32]

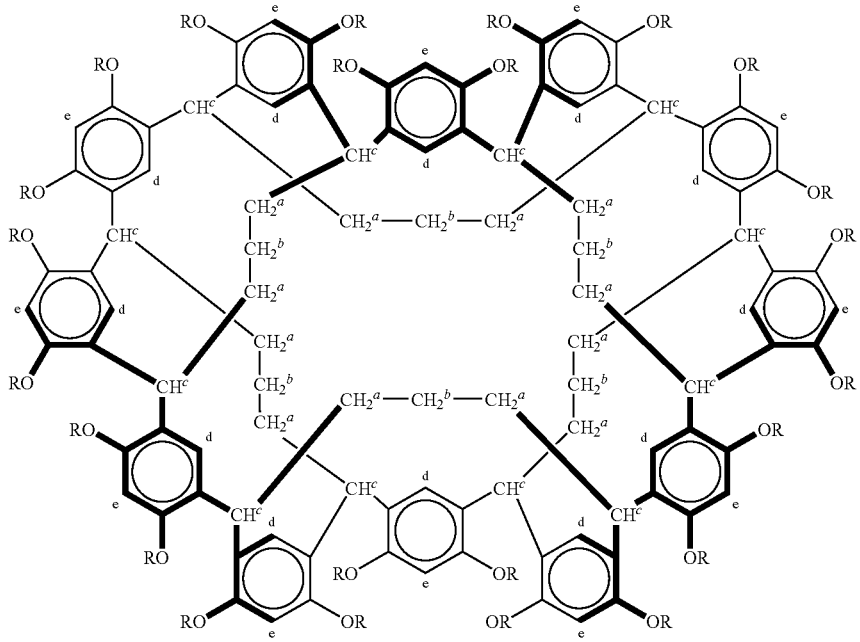

(27)

R: 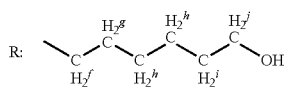

Example 23

Synthesis of Derivative Using 3-chloromethyl-3-ethyloxetane (CMEO) (Introduction of Cationically Polymerizable Group)

0.30 g (0.18 mmol, OH equivalent: 4.22 mmol) of $T_3$ and 0.07 g (0.21 mmol) of TBAB were weighed and dissolved in 9 ml of NMP. Then, after the addition of 0.25 g (10.6 mmol) of sodium hydride, the mixture was stirred at room temperature for one hour. After the salt formation, 1.70 g (12.7 mmol) of CMEO was added, and the mixture was stirred for 48 hours at 80° C. After the reaction, the reaction mixture was diluted with ethyl acetate and washed three times with distilled water. The organic layer was dried over anhydrous magnesium sulfate. After removing the drying agent by filtration, the filtrate was concentrated and reprecipitated using chloroform as a good solvent and n-hexane as a poor solvent to obtain a white powdery solid. The structure of the resulting solid was determined by IR, $^1$H-NMR, and MALDI-TOF-MS. The results are shown below and the structure is shown by the formula (28). In the formula (28), symbols a to i attached to hydrogen atoms correspond to the hydrogen atom symbols in the NMR data. The results confirmed that the etherification rate of the derivative obtained was 100%. The compound shown in the formula (28) is hereinafter referred to as $T_3$-5.

Amount: 0.50 g (70%) IR(KRS): (cm$^{-1}$): 2962 ($v_{CH3}$), 2935 ($v_{CH2}$), 2935 ($v_{CH}$), 1608, 1502, 1460 ($v_{C=C(aromatic)}$), 1292, 1107 ($v_{C-O-C(ether)}$), 980 ($v_{C-O-C(cyclic\ ether)}$) $^1$H-NMR (600 MHz, Solvent DMSO-d$_6$, Internal standard TMS); δ (ppm)=0.68 to 1.91 (m, 52.0H, H$^a$, H$^b$, H$^h$, H$^i$), 3.96 to 4.95 (m, 52.0H, H$^c$, H$^f$, H$^g$), 5.42 to 7.81 (m, 8.00H, H$^e$, H$^d$) Mass spectrometry (MALDI-TOF-MS) Calculated value (m/z): 4098.74 [M+K$^+$] Found value (m/z): 4096.74 [M+K$^+$].

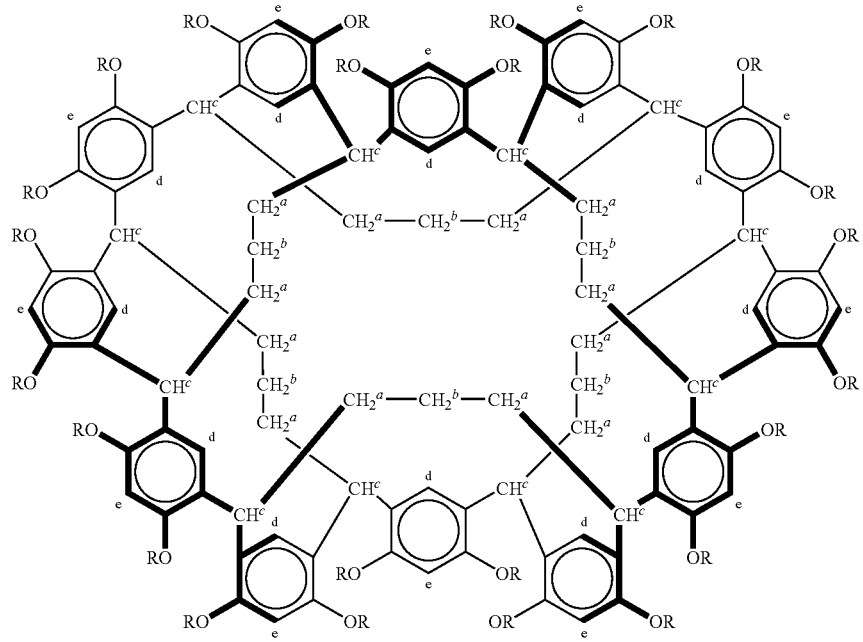

[Formula 33]

(28)

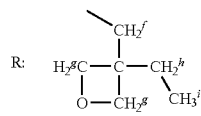

Example 24

Study on the Synthesis Conditions of $T_3$-5)

The derivative $T_3$-5 was synthesized in the same manner as in Example 23, except that the synthesis conditions shown in Table 2 were applied. The yield and etherification rate (measured by $^1$H-NMR) are shown in Table 2.

TABLE 2

| CMEO mmol(OHeq.) | Base | Time (hours) | Etherification (%) | Yield (%) |
|---|---|---|---|---|
| 8.45(2) | Na$_2$CO$_3$ | 48 | 50 | 73 |
| 12.7(3) | Na$_2$CO$_3$ | 48 | 50 | 72 |
| 8.45(2) | Cs$_2$CO$_3$ | 48 | 75 | 40 |
| 12.7(3) | Cs$_2$CO$_3$ | 48 | 80 | 45 |
| 12.7(3) | NaH | 24 | 98 | 70 |
| 12.7(3) | NaH | 48 | 100 | 70 |

Temperature: 80° C.,
TBAB: 5 mol %

When sodium carbonate was used as a base, the etherification rate was 50%, and MALDI-TOF-MS showed that 12-substituted compound was selectively obtained even if the charge ratio was changed. That is, a predetermined number of OH groups can be preserved by selecting reaction conditions, and the functional groups can be complexed by introducing other functional groups into the remaining OH groups.

Example 25

Synthesis of Derivative Using 2-chloroethyl vinyl ether (CEVE) (Introduction of Radically Polymerizable Group)

1 g (0.58 mmol, OH equivalent: 14.4 mmol) of $T_3$ and 0.23 g (0.70 mmol) of TBAB were weighed and dissolved in 15 ml of NMP. Then, after the addition of 0.68 g (28.8 mmol) of sodium hydride, the mixture was stirred at room temperature for one hour. After the salt formation, 3.00 g (28.8 mmol) of 2-chloroethyl vinyl ether was added, and the mixture was stirred for 48 hours at 80° C. After the reaction, the reaction mixture was diluted with ethyl acetate and washed three times with distilled water. The organic layer was dried over anhydrous magnesium sulfate. After removing the drying agent by filtration, the filtrate was concentrated and reprecipitated using chloroform as a good solvent and methanol as a poor solvent to obtain a white powdery solid. The structure of the resulting solid was determined by IR, $^1$H-NMR, and MALDI-TOF-MS. The results are shown below, and the structure is shown by the formula (29). In the formula (29), symbols a to i attached to hydrogen atoms correspond to the hydrogen atom symbols in the NMR data. The results confirmed that the etherification rate of the derivative obtained was 100%. The compound shown in the formula (29) is hereinafter referred to as $T_3$-6. As a result of analysis of the stereostructure and molecule movement of $T_3$-6, it was confirmed that proximate molecules are very close to each other forming a channel structure. This suggests self-association due to the strong p-p stacking of a vinyl group and a benzene ring. Thus, it was confirmed that high molecular weight molecules easily crystallize with the application of self-association. If a conductive polymer is located in the channel by utilizing the channel structure, very minute conductive channels surrounded by the insulating calixarene compound can be formed and applied to various fields such as the field of ultrafine electronic circuit.

Figure 6:
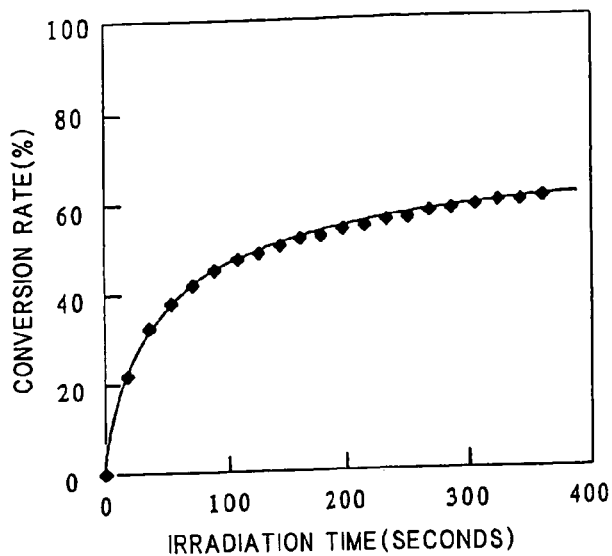
FIG. 6 is a graph showing the change in the conversion rate due to the photo cationic reaction of $T_3$-5 in Example 26.
Figure 7:
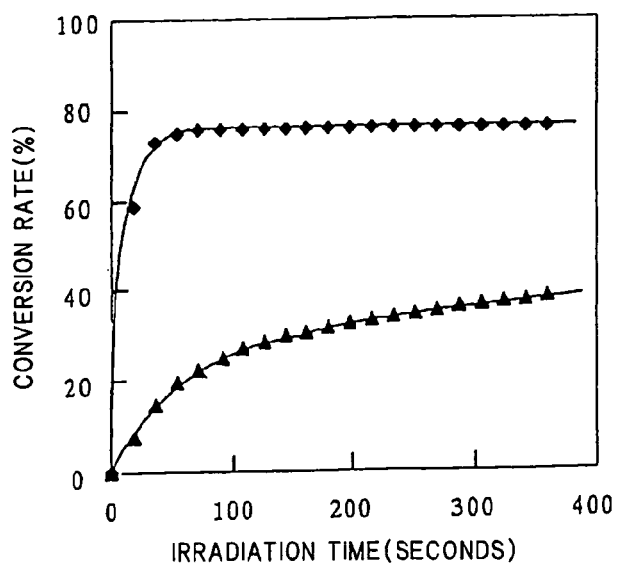
FIG. 7 is a graph showing the change in the conversion rate due to the photo cationic reaction of $T_3$-6 in Example 26.
Figure 8:
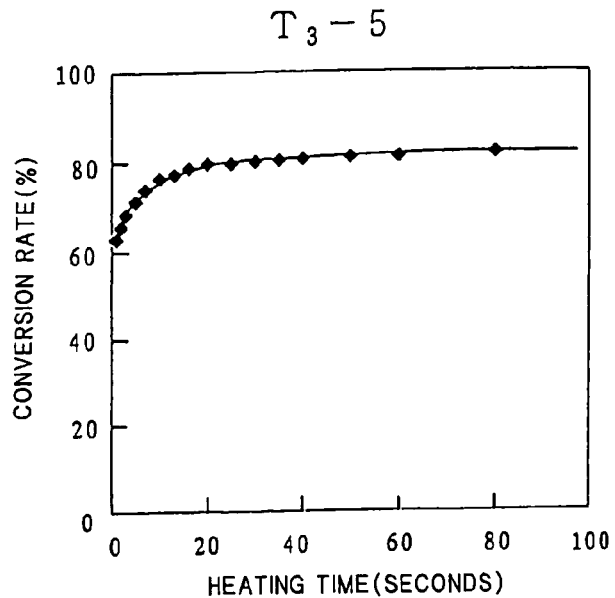
FIG. 8 is a graph showing the change in the conversion rate due to heating after the photo cationic reaction of $T_3$-5 in Example 26.
Figure 9:
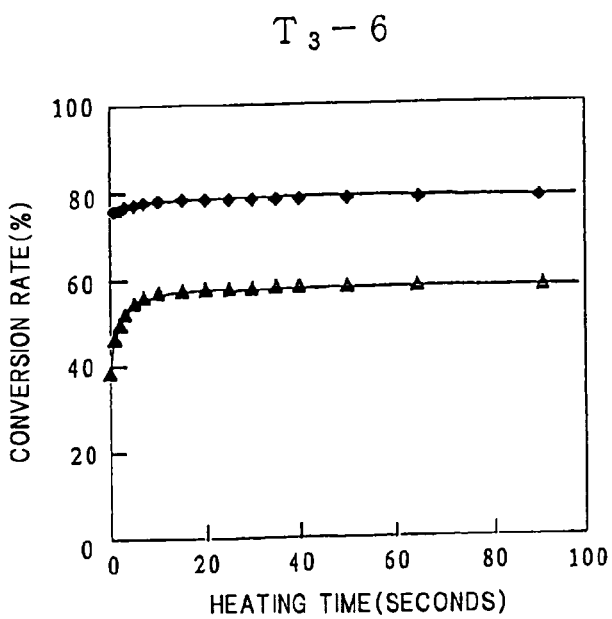
FIG. 9 is a graph showing the change in the conversion rate due to heating after the photo cationic reaction of $T_3$-6 in Example 26.

Amount: 1.54 g (78%) IR(KRS): (cm$^{-1}$): 2939 ($v_{CH}$), 1617 ($v_{C=C}$), 1500, 1455 ($v_{C=C(aromatic)}$), 1294, 1158 ($v_{C-O-C}$), 1005 ($v_{=C-O-C}$) $^1$H-NMR (600 MHz, Solvent DMSO-d$_6$, Internal standard TMS); d (ppm)=0.28 to 1.37 (m, 4.00H, H$^b$), 1.37 to 2.37 (m, 8.00H, H$^a$), 3.65 to 4.75 (m, 52. OH, H$^c$, H$^f$ H$^g$, H$^i$, H$^{i'}$), 6.00 to 7.50 (m, 16.0H, H$^e$, H$^d$, H$^h$) Mass spectrometry (MALDI-TOF-MS) Calculated value (m/z): 3387.30 [M] Found value (m/z): 3387.44 [M].

residue (T$_3$-5) or vinyl ether residue (T$_3$-6) on the basis of the absorption peak of phenyl group using FT-IR. The results are shown in FIGS. 6 and 7. In addition, the temperature effect was examined by heating a film irradiated with light for 360 seconds at 150° C. The results are shown in FIGS. 8 and 9.

In T$_3$-6 having vinyl ether group, irradiation decreased the peak at 1,617 cm$^{-1}$ due to the vinyl group. In addition, the fact that the absorption peak at 1,293 cm$^{-1}$ due to vinyl ether shifted to 1,187 cm$^{-1}$ and that the absorption peak due to ether increased indicates the progress of the target cationic polymerization. The cationic photopolymerization quickly advanced, and the conversion rate reached 80% (5 mol % DPSP) and 40% (1 mol % DPSP) by irradiation for 360 seconds. In the system where 5 mol % of DPSP was added, almost all vinyl ethers polymerized, and the molecule motil-

[Formula 34]

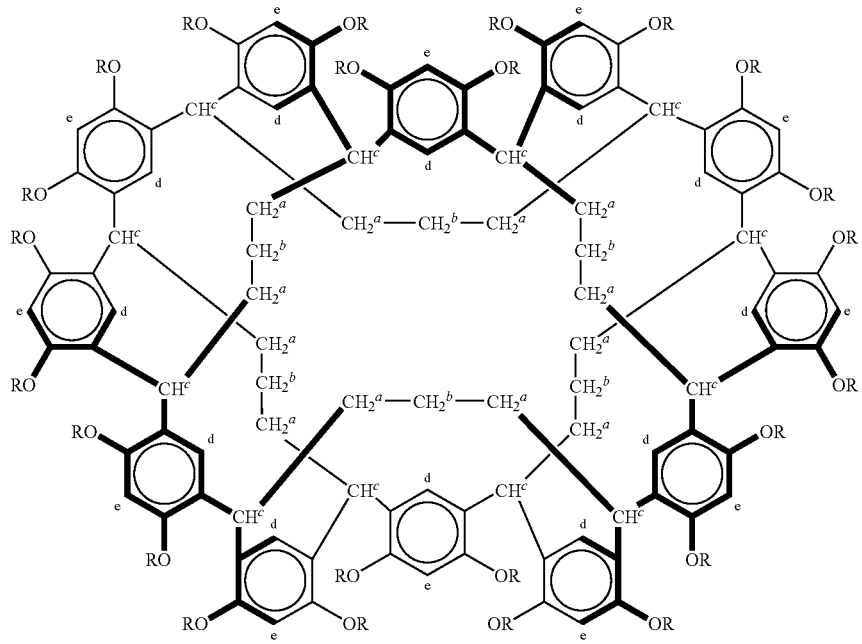

(29)

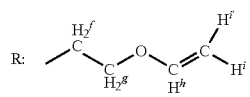

Example 26

Cationic Photopolymerization of T$_3$-5 and T$_3$-6

To T$_3$-5 having oxetane and T$_3$-6 having vinyl ether were added bis[4-(diphenylsulfonio)phenyl]sulfide-bis(hexafluorophosphate) (hereinafter referred to as DPSP) as a photoacid generator respectively in an amount of 1 mol % or 5 mol % for the functional group. The mixture was dissolved in chloroform and applied to a KBr board. The coating was dried at room temperature and the coating in the form of a film was irradiated with light from a ultra high pressure mercury lamp (wavelength: 360 nm, intensity: 15 mW/cm$^2$) to effect cationic photopolymerization. The conversion rate was calculated from the reduction of the absorption peak of cyclic ether ity decreased so that the conversion rate did not improve even when the system was heated to 150° C.

The cationic photopolymerization of T$_3$-5 having oxetane quickly advanced, and the conversion rate reached 60% (5 mol % DPSP) by irradiation for 360 seconds. In addition, the conversion rate increased to 80% by heating the film which had been irradiated with light. In the same manner as in T$_3$-6, the molecule motility decreased so that the conversion rate did not improve even if the system was heated to 150° C.

Example 27

Photopolymerization of T$_3$-6

T$_3$-6 with the etherification rate of 100% was photocured in the same manner as in Example 16. The conversion rate was

Example 28

Devinylation of T$_3$-6

0.50 g (0.15 mmol, OH equivalent: 3.55 mmol) of T$_3$-6 was weighed and completely dissolved in a mixed solvent of 4:1 (v/v) ether and methylene chloride. After the addition of 0.35 ml (4.26 mmol) of 12N hydrochloric acid was dropped, the mixture was stirred for five minutes at room temperature. Then, a large amount of ether was added. The precipitate was filtered and washed three times with a mixed solvent of ether and methanol to obtain a greenish brown powdery solid. The structure of the resulting solid was determined by IR and $^1$H-NMR. The results are shown below, and the structure is shown by the formula (30). In the formula (30), symbols a to j attached to hydrogen atoms correspond to the hydrogen atom symbols in the NMR data. The results confirmed that the vinyl groups have been completely eliminated from the solid and converted into hydroxylethyl groups. The compound shown in the formula (30) is hereinafter referred to as T$_3$-7.

Amount: 0.37 g (91%) IR(KRS): (cm$^{-1}$): 3367 ($\nu_{OH}$), 2929 ($\nu_{CH}$), 1499, 1450 ($\nu_{C=C(aromatic)}$), 1293, 1187 ($\nu_{C-O-C}$) $^1$H-NMR (600 MHz, Solvent DMSO-d$_6$, Internal Standard TMS); δ (ppm)=0.18 to 2.31 (m, 12.0H, H$^a$, H$^b$), 3.25 to 5.94 (m, 36.0H, H$^c$, H$^f$, H$^g$), 6.50 to 8.30 (m, 8.00H, H$^e$, H$^d$)

Example 29

Introduction of β-Methacryloyl) Ethoxy Group)

A rotor was put into a 50 ml three-necked flask, and 1.38 g (0.5 mmol, OH equivalent: 24 mmol) of T$_3$-7 was weighed and dissolved in 5.69 g (72 mmol) of pyridine. Then, after the addition of 7.39 g (48 mmol) of methacrylic acid anhydride (MAA) dropwise in a nitrogen atmosphere, the mixture was stirred at room temperature for 24 hours. After the reaction, the reaction mixture was diluted with chloroform and washed twice with an aqueous solution of sodium hydrogencarbonate, then twice with distilled water. The organic layer was dried over anhydrous magnesium sulfate. After removing the drying agent by filtration, the filtrate was concentrated and reprecipitated using chloroform as a good solvent and ether as a poor solvent. The precipitate was collected and dried at room temperature under reduced pressure. As a result, a white powdery solid was obtained. The structure of the resulting powdery solid was determined by IR and $^1$H-NMR. The results are shown below, and the structure is shown by the formula (31). In the formula (31), symbols a to i attached to hydrogen atoms correspond to the hydrogen atom symbols in the NMR data. The results confirmed that the esterification was 100%, that MAA was condensed with the OH group of hydroxylethyl group, and that (β-methacryloyl)ethoxy group was introduced. The compound shown in the formula (31) is hereinafter referred to as T$_3$-8.

[Formula 35]

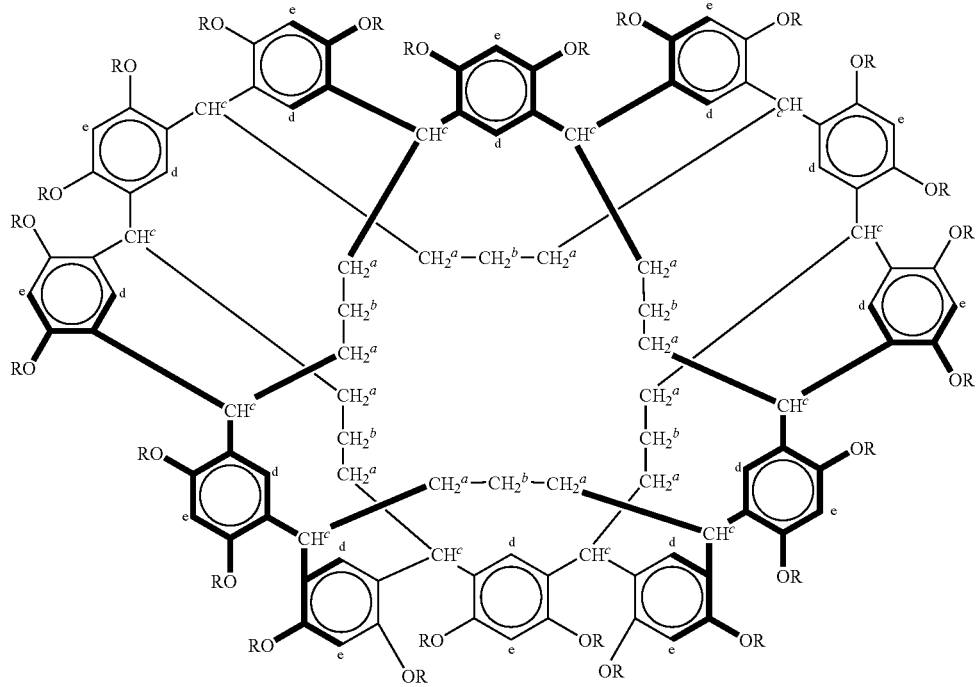

(30)

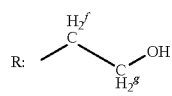

Amount: 2.23 g (72%) IR(KRS): (cm$^{-1}$): 2929 ($\nu_{CH}$), 1719 ($\nu_{C=O(ester)}$), 1636 ($\nu_{C=C(methacryl)}$) 1501 ($\nu_{C=C(aromatic)}$), 1295, 1164($\nu_{C-O-C}$) $^1$H-NMR (500 MHz, Solvent DMSO-d$_6$, Internal standard TMS); δ (ppm)=1.64 to 2.45 (m, 28.0H, H$^a$, H$^b$, H$^h$), 3.40 to 5.11 (m, 36.0H, H$^c$), 5.58 to 8.43 (m, 24.0H, H$^e$, H$^d$, H$^i$, H$^{i'}$)
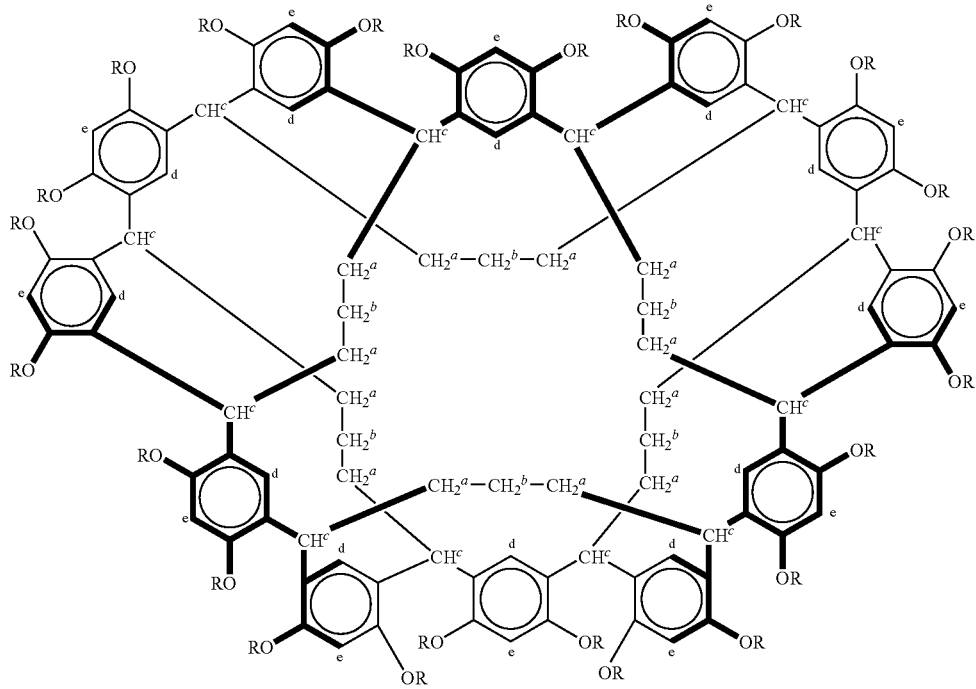
[Formula 36]
(31)
R: 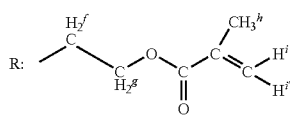

Example 30

Photo-Cure Reaction of $T_3$-8

$T_3$-8 was photo-cured in the same manner as in Examples 16 and 17. As a result, the compound cross-linked to achieve a conversion rate of about 40%, indicating that the photo reactivity was higher than $T_3$-1 but lower than $T_3$-2. The reason for the higher photo reactivity than $T_3$-1 is considered to be due to the higher molecule motility of methacryloyl groups than $T_3$-1, and the reason for the lower photo reactivity than $T_3$-2 is considered to be due to the absence of hydroxyl groups unlike $T_3$-2.

Example 31

Synthesis of Hybrid-Type Derivative Using CMEO and MAC

MAC was reacted in the same manner as in Example 1 except for using a CMEO derivative with an etherification rate of 50% obtained by using sodium carbonate as a base in Example 24. The structure of the resulting white powdery solid was determined by IR and $^1$H-NMR. The results are shown below, and the structure is shown by the formula (32). In the formula (32), symbols a to k attached to hydrogen atoms correspond to the hydrogen atom symbols in the NMR data. The results confirmed that the obtained derivative was a hybrid type derivative in which all remaining hydroxyl groups have been esterified, with 50% of substituents originating from CMEO and 50% of substituents originating from MAC having been introduced. The compound shown in the formula (32) is hereinafter referred to as $T_3$-9.

Amount: 1.62 g (86%) IR(KRS): (cm$^{-1}$): 2962 ($\nu_{CH3}$), 2932 ($\nu_{CH2}$), 2870 ($\nu_{CH}$), 1735 ($\nu_{C=O(ester)}$), 1637 ($\nu_{C=C(methacryl)}$) 1611, 1498, 1458($\nu_{C=C(aromatic)}$), 1293, 1131 ($\nu_{C-O-C(ether)}$), 982 ($\nu_{C-O-C(cyclic\ ether)}$) $^1$H-NMR (600 MHz, Solvent CDCl$_3$, Internal standard TMS); δ (ppm)= 0.68 to 1.27 (m, 20. OH, H$^f$, H$^g$), 1.55 to 2.62 (m, 24.0H, H$^a$, H$^b$, H$^j$), 3.00 to 5.20 (m, 28.0H, H$^c$, H$^e$, H$^d$), 5.48 to 6.20 (m, 8.0H, H$^k$, H$^{k'}$), 6.32 to 7.24, 7.27 to 7.75 (m, 8.0H, H$^h$, H$^i$)

[Formula 37]

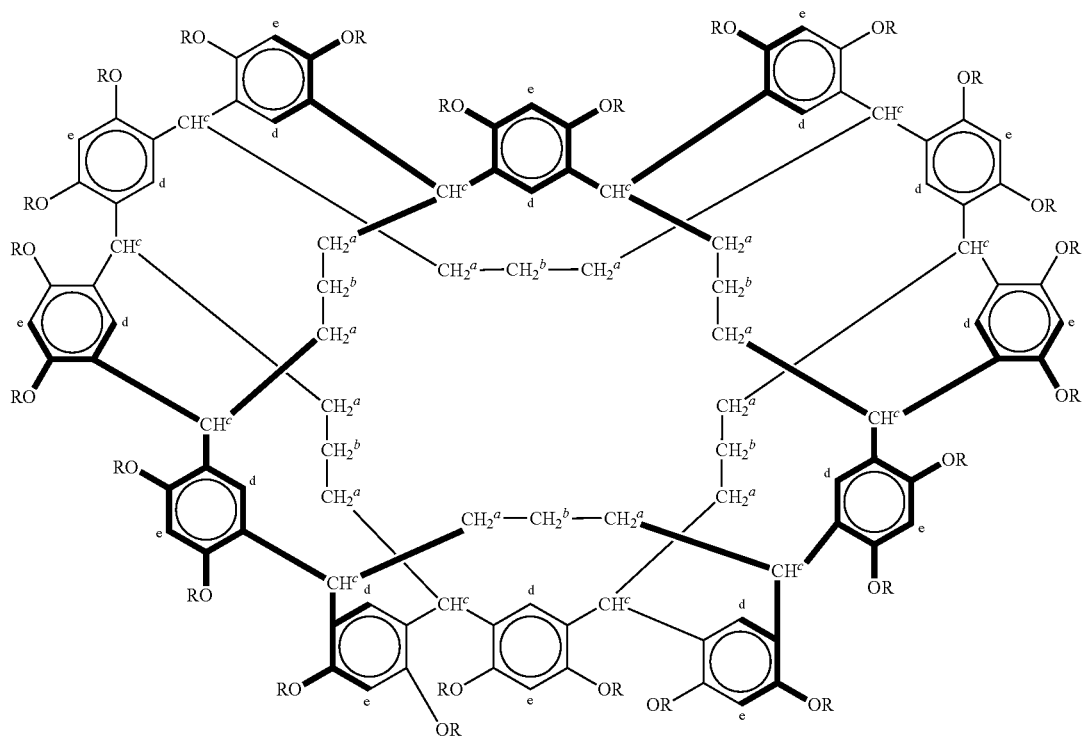

(32)

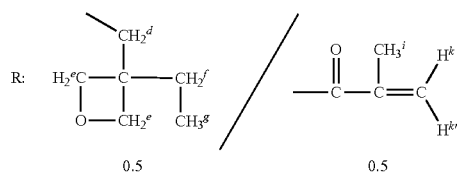

Example 32

Evaluation of Thermal Characteristics

TG/DTA and DSC were used for the determination of the decomposition initiation temperature, 5% mass reduction temperature, and glass transition temperature of the derivatives shown in Table 3. The results are shown in Table 3. The glass transition temperature could not be determined in any of the compounds. All compounds were confirmed to have high heat resistance. Comparison of $T_3$ with $T_3$-7 in which vinyl ether was deprotected and a spacer was introduced confirmed that there were almost no changes in the decomposition initiation temperature and 5% mass reduction temperature caused by introduction of the spacer. The lower decomposition initiation temperatures of these compounds as compared with other derivatives are due to their slight acidity resulting from the hydroxyl groups. $T_3$ having phenolic hydroxyl groups had a lower decomposition initiation temperature. $T_3$-2a decomposed in two stages, that is, first the decomposition of phthalic acid ester bond and second the decomposition of the ester bond of methacryloyl groups. The decomposition initiation temperature caused by methacryloyl groups showed good correlation with the decomposition initiation temperature of $T_3$-2.

TABLE 3

| $T_3$ derivative | Rate of esterification or etherification (%) | First decomposition temperature (° C.)(*1) Decomposition initiation temperature | First decomposition temperature (° C.)(*1) 5% mass decomposition temperature | Second decomposition temperature (° C.)(*2) |
|---|---|---|---|---|
| $T_3$ | 0 | 333 | 365 | — |
| $T_3$-1 | 100 | 387 | 418 | — |
| $T_3$-2 | 100 | 332 | 365 | — |
| $T_3$-2a | 100 | 196 | 226 | 320 |
| $T_3$-6 | 100 | 336 | 365 | — |
| $T_3$-5 | 100 | 347 | 387 | — |
| $T_3$-7 | 100 | 375 | 348 | — |
| $T_3$-8 | 100 | 348 | 390 | — |
| $T_3$-9 | 100 | 358 | 390 | — |

(*1)Measured using TG/DTA in a nitrogen atmosphere at a temperature rise of 10° C./min
(*2)Measured using DSC in a nitrogen atmosphere at a temperature rise of 10° C./min

Example 33

Solubility Test

A solubility test was carried out by adding 2 ml of each of the solvents shown in Table 4 to 2 mg of each of the derivatives listed in Table 4. The results are shown in Table 4. Modification with hydroxyl groups was confirmed to increase the solubility and provide the derivatives with sufficient film-formability.

TABLE 4

| Solvent | $T_3$ | $T_3$-1 | $T_3$-2 | $T_3$-2a | $T_3$-6 | $T_3$-5 | $T_3$-7 | $T_3$-8 | $T_3$-9 |
|---|---|---|---|---|---|---|---|---|---|
| Water | − | − | − | − | − | − | − | − | − |
| Methanol | − | − | ++ | ++ | − | ++ | − | − | +− |
| 2-Propanol | − | +− | +− | +− | +− | ++ | − | − | + |
| n-Hexane | − | − | − | − | − | − | − | − | − |
| Acetone | − | ++ | ++ | ++ | ++ | ++ | − | ++ | ++ |
| Chloroform | − | ++ | ++ | ++ | ++ | ++ | − | ++ | ++ |
| THF | +− | ++ | ++ | ++ | ++ | ++ | − | ++ | ++ |
| DMF | ++ | ++ | ++ | ++ | ++ | ++ | ++ | ++ | ++ |
| NMP | ++ | ++ | ++ | ++ | ++ | ++ | ++ | ++ | ++ |
| DMSO | ++ | ++ | ++ | ++ | ++ | ++ | ++ | ++ | ++ |
| PGMEA | − | ++ | ++ | + | ++ | ++ | − | ++ | ++ |
| 2-Heptanone | − | ++ | + | + | ++ | ++ | − | ++ | ++ |
| Film-formability | x | o | o | o | o | o | x | o | o |

Solubility
++: soluble at room temperature,
+: soluble after heating,
+−: partially soluble,
−: insoluble
Film formability
o: film formation possible,
x: film formation not possible
(Cast solvent: chloroform)

Example 43

Synthesis of Calixarene-Cavitant

A calixarene compound was prepared according to the method of Example 1 using methyl resorcinol and glutaraldehyde as raw materials. 0.46 g (0.25 mmol, OH equivalent: 6 mmol) of this compound, 0.82 g (6.5 mmol) of $K_2CO_3$, and 0.01 g (0.05 mol % of the OH equivalent) of TBAB were dissolved in 4 ml of N-methylpyrrolidone. The mixture was stirred at 50° C. for three hours. Next, 1.55 g (8 mmol) of dibromomethane was added, and the mixture was stirred for 24 hours at 80° C. After the reaction, the reaction solution was poured into 0.1 M aqueous solution of hydrochloric acid to collect precipitate. The precipitate collected by filtration was washed with distilled water, and dried under reduced pressure to obtain a light brown solid. The obtained solid was dissolved in methylene chloride and subjected to silica-gel column chromatography (developer: $CH_2Cl_2$) to isolate a white solid. The structure was determined by IR, MALDI-TOF-MS, and $^1$H-NMR. The analytical results confirmed that the derivative obtained had a structure shown by the formula (33). In the formula (33), symbols a to f attached to hydrogen atoms correspond to the hydrogen atom symbols in the NMR data. This derivative was dissolved in acetone and methylene chloride.

Amount: 0.106 g (21%) IR(KRS): (cm$^{-1}$) 2933 ($v_{C-H}$), 1477 ($v_{C=C(aromatic)}$) 1094($v_{C-O-C}$) $^1$H-NMR (600 MHz, Solvent CDCl$_3$, Internal standard TMS); δ (ppm)=1.72 to 1.97 (m, 24.0H, H$^a$, H$^b$, H$^e$), 4.26 (br s, 4.0H, H$^f$), 4.83 to 5.01 (m, 4.0H, H$^c$), 5.87 (br s, 4.0H, H$^f$), 6.98 to 7.21 (m, 4.0H, H$^d$) MALDI-TOF-MS Calculated value (m/z): 2015.96 [M+H]$^+$ Found value (m/z): 2016.12 [M+H]$^+$.

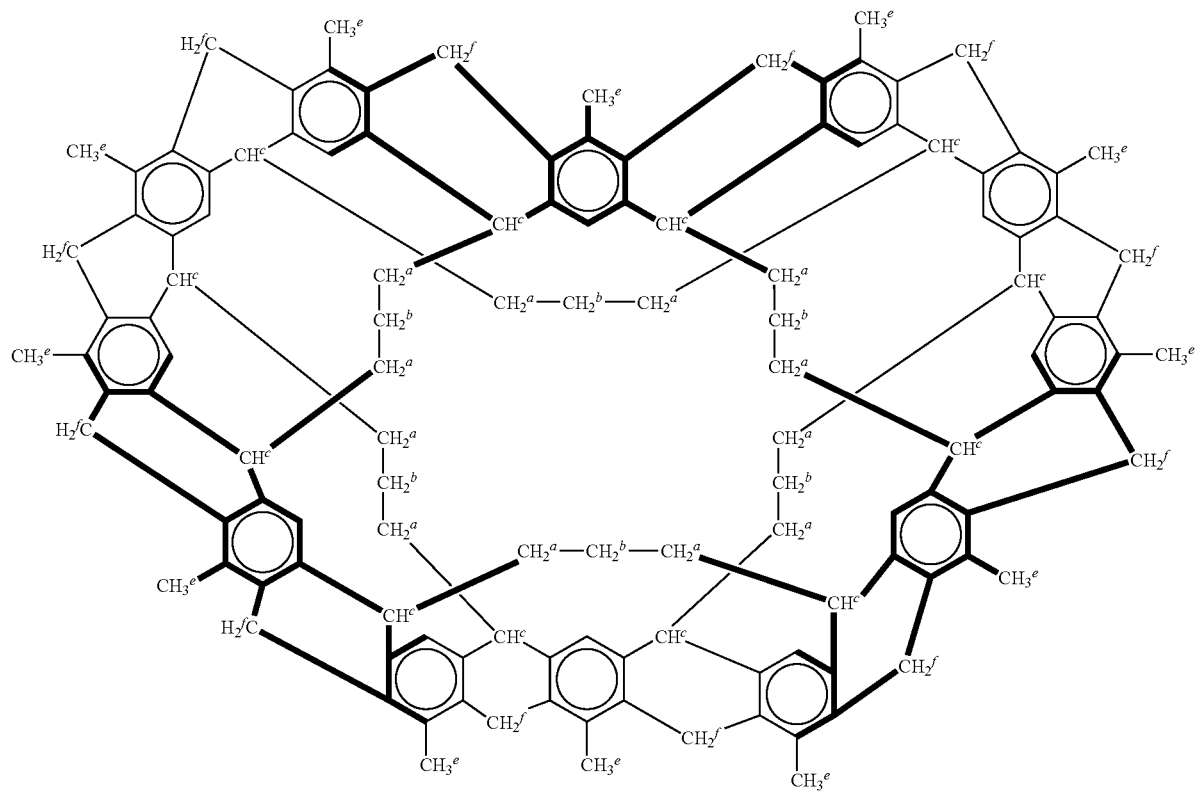

(33)

INDUSTRIAL APPLICABILITY

As described above, the calixarene compounds of the present invention are expected to be useful as inclusion compounds. The calixarene derivatives provided with functions by introducing functional groups have high heat resistance and are expected to be useful in curable compositions and resist compositions, as inclusion compounds, and in a wide variety of fields such as application as intermediates for producing calixarene derivatives possessing higher functions. The manufacturing method of the present invention can easily produce such compounds. The intermediate compounds of the present invention can suitably be used as raw materials of such compounds. Since the composition containing the calixarene derivatives can produce films with high heat resistance due to its improved film-formability, the composition can be used for a wide variety of applications such as a photoresist.

The invention claimed is:

1. A calixarene compound shown by following formula (1):

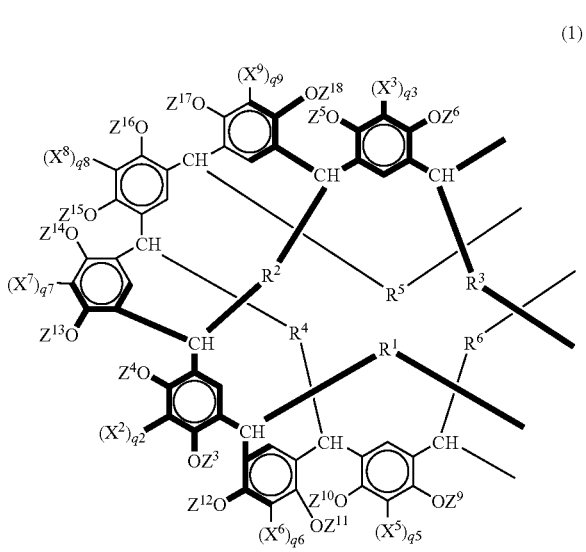

(1)

-continued

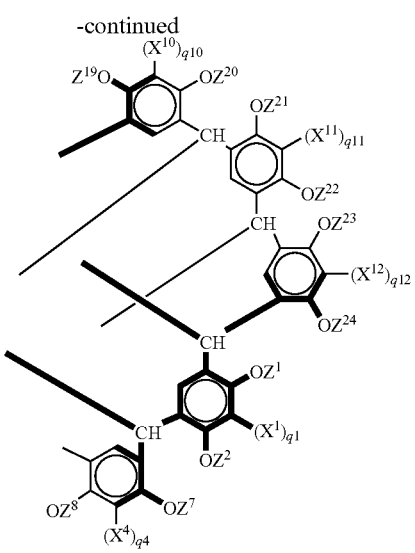

wherein $R^1$ to $R^6$ individually represent a substituted or unsubstituted alkylene group having 1 to 8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content, or two adjacent Zs in combination represent a substituted or unsubstituted alkylene group having 1 to 8 carbon atoms; $q^1$ to $q^{12}$ individually represent an integer of 0 or 1.

2. The calixarene compound according to claim 1, wherein $X^1$ to $X^{12}$ in the formula (1) are methyl groups.

3. The calixarene compound according to claim 1, wherein $q^1$ to $q^{12}$ in the formula (1) are 0.

4. The calixarene compound according to claim 1, wherein $R^1$ to $R^6$ are individually an alkylene group having 3, 5, 7, or 8 carbon atoms.

5. The calixarene compound according to claim 1, wherein all of the $Z^1$ to $Z^{24}$ groups in the formula (1) are hydrogen atoms.

6. The calixarene compound according to claim 1, wherein at least one of the $Z^1$ to $Z^{24}$ groups in the formula (1) is a group other than hydrogen atom.

7. The calixarene compound according to claim 6, wherein at least one of the $Z^1$ to $Z^{24}$ groups in the formula (1) has a polymerizable functional group.

8. The calixarene compound according to claim 7, wherein the polymerizable functional group is a polymerizable unsaturated group and/or a cyclic ether group.

9. The calixarene compound according to claim 6, wherein at least one of the $Z^1$ to $Z^{24}$ groups in the formula (1) has an alkali-soluble group.

10. The calixarene derivative according to claim 9, wherein the alkali-soluble group is at least one group selected from the group consisting of a carboxyl group, amino group, sulfonamide group, sulfonic acid group, and phosphoric acid group.

11. The calixarene derivative according to claim 6, wherein at least one of the groups among $Z^1$ to $Z^{24}$ in the formula (1) has both a polymerizable functional group and an alkali-soluble group.

12. At least one intermediate of a calixarene compound of the following formulae (3), to (8):

(3)

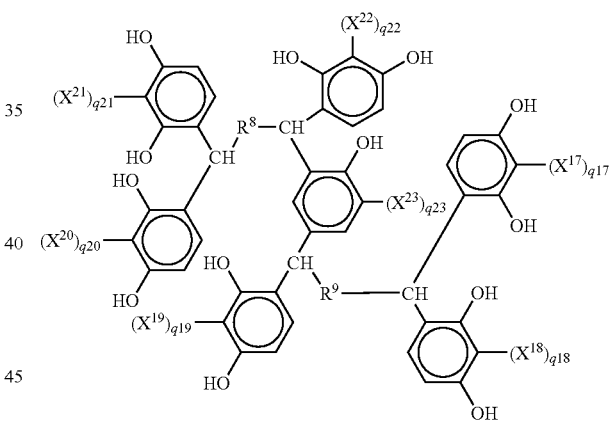

wherein $R^8$ and $R^9$ individually represent a substituted or unsubstituted alkylene group having 1 to 8 carbon atoms; $X^{17}$ to $X^{23}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{17}$ to $q^{23}$ individually represent an integer of 0 or 1, (4)

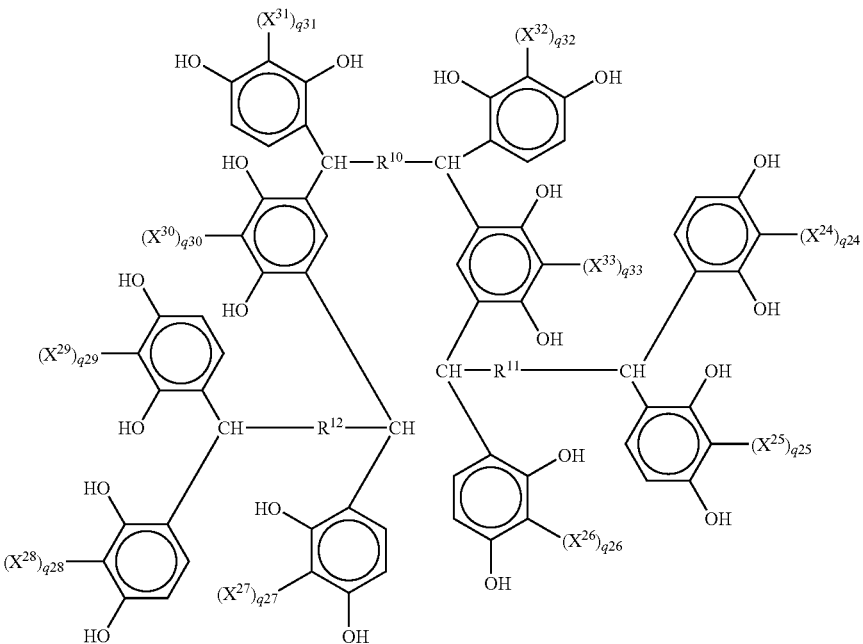

wherein $R^{10}$ to $R^{12}$ individually represent a substituted or unsubstituted alkylene group having 1 to 8 carbon atoms; $X^{24}$ to $X^{33}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $q^{24}$ to $q^{33}$ individually represent an integer of 0 or 1, (5)

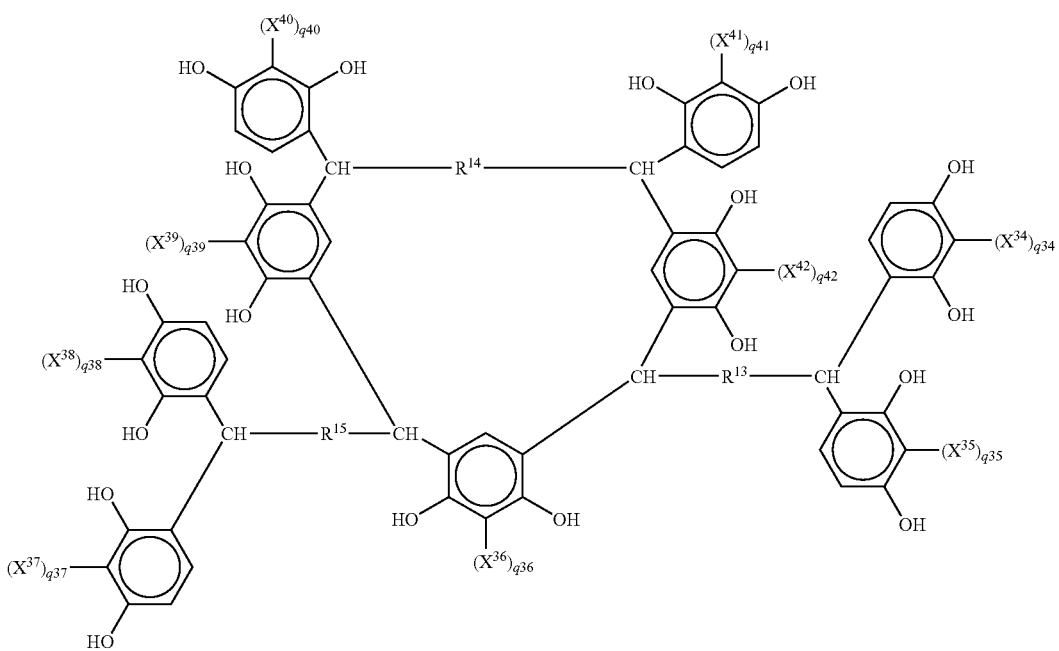

wherein $R^{13}$ to $R^{15}$ individually represent a substituted or unsubstituted alkylene group having 1 to 8 carbon atoms; $X^{34}$ to $X^{42}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{34}$ to $q^{42}$ individually represent an integer of 0 or 1,

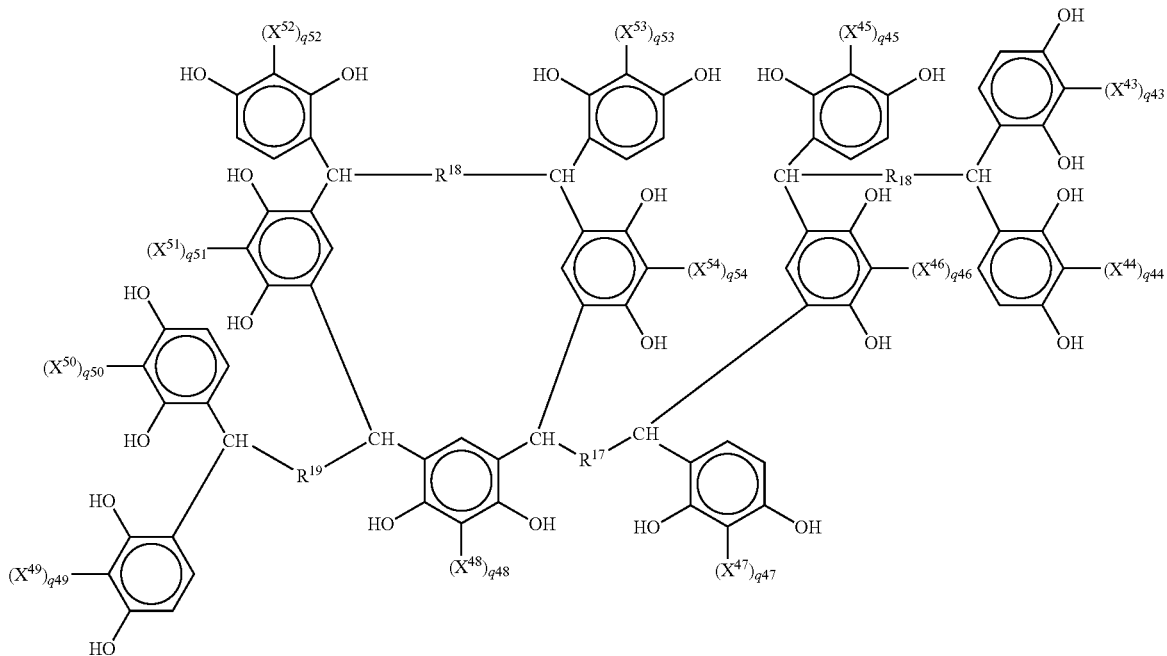

(6)

wherein $R^{16}$ to $R^{19}$ represent a substituted or unsubstituted alkylene group having 1 to 8 carbon atoms; $X^{43}$ to $X^{54}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{43}$ to $q^{54}$ individually represent an integer of 0 or 1,

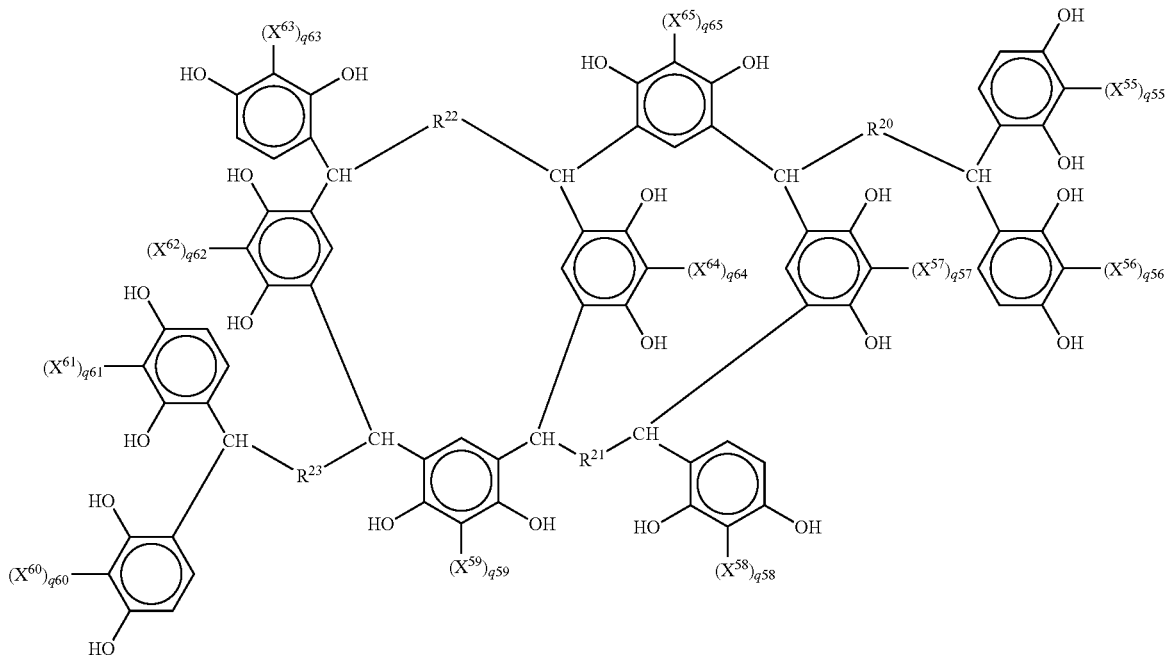

(7)

wherein $R^{20}$ to $R^{23}$ represent a substituted or unsubstituted alkylene group having 1 to 8 carbon atoms; $X^{55}$ to $X^{65}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{55}$ to $q^{65}$ individually represent an integer of 0 or 1, (8)
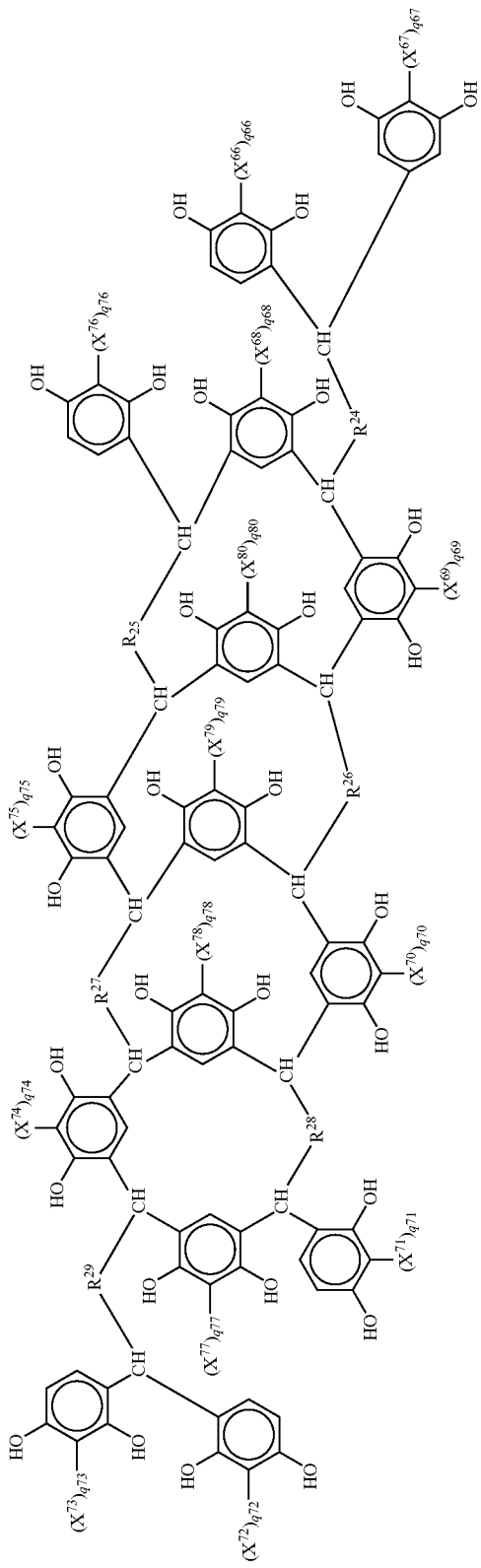

wherein $R^{24}$ to $R^{29}$ represent a substituted or unsubstituted alkylene group having 1 to 8 carbon atoms; $X^{66}$ to $X^{80}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{66}$ to $q^{80}$ individually represent an integer of 0 or 1.

13. The intermediate of a calixarene compound according to claim 12, wherein $X^{17}$ to $X^{80}$ in the formulas (3) to (8) are methyl groups.

14. The intermediate of a calixarene compound according to claim 12, wherein $q^{17}$ to $q^{80}$ in the formulas (3) to (8) are 0.

15. The intermediate of a calixarene compound according to claim 12, wherein $R^8$ to $R^{29}$ in the formulas (3) to (8) are individually an alkylene group having 3, 5, 7, or 8 carbon atoms.

16. A method for manufacturing a calixarene compound comprising condensing at least one compound of formula (9) and at least one compound of formula (10):

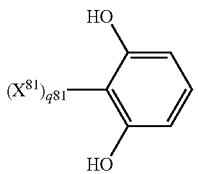

(9)

wherein $X^{81}$ represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; and $q^{81}$ is an integer of 0 or 1, $$OHC—R^{30}—CHO \quad (10)$$

wherein $R^{30}$ represents a substituted or unsubstituted alkylene group having 1 to 8 carbon atoms.

17. The method according to claim 16, wherein $X^{81}$ in the formula (9) is a methyl group.

18. The method according to claim 16, wherein $q^{81}$ in the formula (9) is 0.

19. The method according to claim 16, wherein $R^{30}$ in the formula (10) is an alkylene group having 3, 5, 7, or 8 carbon atoms.

20. A composition comprising a calixarene compound of claim 1 and a solvent which dissolves the calixarene compound of the formula (1):

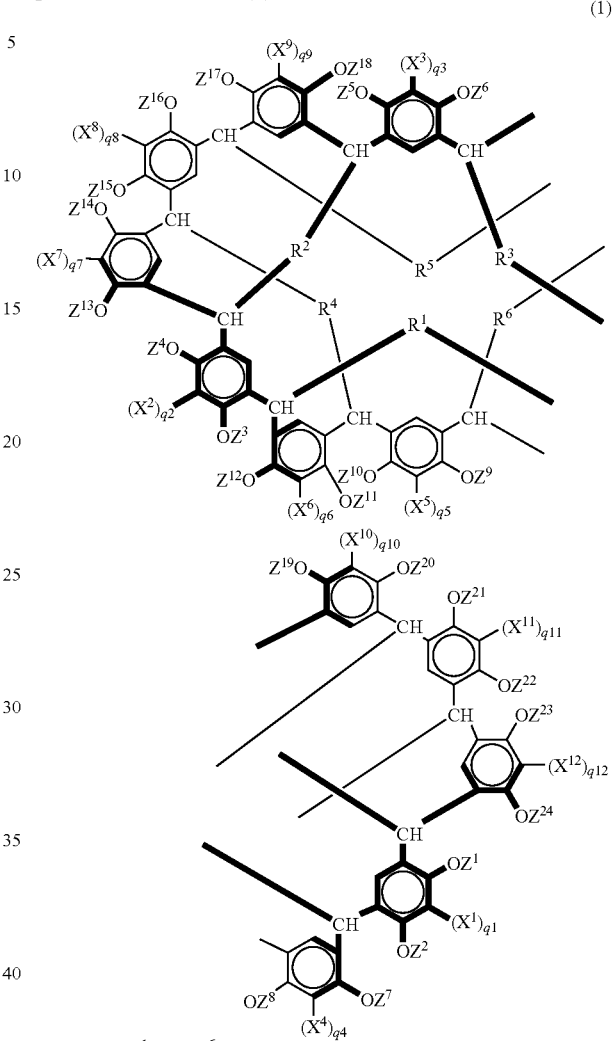

(1)

wherein $R^1$ to $R^6$ individually represent a substituted or unsubstituted alkylene group having 1-8 carbon atoms; $X^1$ to $X^{12}$ individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxyl group having 1 to 10 carbon atoms, or a substituted or unsubstituted phenoxy group; $Z^1$ to $Z^{24}$ individually represent a hydrogen atom, a group having a polymerizable functional group, a group having an alkali-soluble group, or a substituted alkyl group having an alkyl chain with a 1 to 8 carbon atom content, or two adjacent Zs in combination represent a substituted or unsubstituted alkylene group having 1 to 8 carbon atoms; $q^1$ to $q^{12}$ individually represent an integer of 0 or 1.

21. The composition according to claim 20, wherein the calixarene compound has a polymerizable functional group for at least one of the $Z^1$ to $Z^{24}$ groups in the formula (1) and the composition further comprises a polymerization initiator.

22. The composition according to claim 20, wherein the calixarene compound has an alkali-soluble group for at least one of the $Z^1$ to $Z^{24}$ groups in the formula (1).

* * * * *